United States Patent
Gokaraju et al.

(10) Patent No.: US 8,748,598 B2
(45) Date of Patent: Jun. 10, 2014

(54) ANALOGS OF 3-O-ACETYL-11-KETO-BETA-BOSWELLIC ACID

(75) Inventors: Ganga Raju Gokaraju, Andhra Pradesh (IN); Rama Raju Gokaraju, Andhra Pradesh (IN); Venkata Subbaraju Gottumukkala, Andhra Pradesh (IN); Trimurtulu Golakoti, Andhra Pradesh (IN); Krishanu Sengupta, Andhra Pradesh (IN)

(73) Assignee: Laila Nutraceuticals (IN)

( * ) Notice: Subject to any disclaimer, the term of this patent is extended or adjusted under 35 U.S.C. 154(b) by 206 days.

(21) Appl. No.: 13/250,841

(22) Filed: Sep. 30, 2011

(65) Prior Publication Data

US 2012/0035176 A1 Feb. 9, 2012

Related U.S. Application Data

(60) Continuation-in-part of application No. 12/549,663, filed on Aug. 28, 2009, now abandoned, which is a division of application No. 10/540,257, filed as application No. PCT/IN2004/000176 on Jun. 18, 2004, now Pat. No. 7,625,947.

(51) Int. Cl.
- *C07D 295/18* (2006.01)
- *C07D 241/04* (2006.01)
- *C07C 61/22* (2006.01)
- *C07C 69/74* (2006.01)
- *C07D 233/54* (2006.01)

(52) U.S. Cl.
USPC ............ 544/172; 544/358; 548/335.1; 560/6; 562/498

(58) Field of Classification Search
USPC ............... 514/510, 766; 560/6; 544/172, 358; 548/335.1; 562/498
See application file for complete search history.

(56) References Cited

U.S. PATENT DOCUMENTS

| | | | |
|---|---|---|---|
| 6,174,876 B1 | 1/2001 | Simmet et al. | |
| 6,534,086 B1 | 3/2003 | Krumhar | |
| 6,589,516 B1 | 7/2003 | Eyre et al. | |

FOREIGN PATENT DOCUMENTS

JP 04288095 A 10/1992

OTHER PUBLICATIONS

International Search Report for PCT/IN2004/000176, mailed on Mar. 18, 2005.
Savoir et al., Triterpenes. XI. Presence of 11-keto-B-boswellic acid in Incense, 1967, bulletin des Brussels chimiques Belges, 76(5-6), 368-370, (two pages of abstract).

*Primary Examiner* — Taylor Victor Oh
(74) *Attorney, Agent, or Firm* — Rader, Fishman & Grauer PLLC

(57) ABSTRACT

Analogs of 3-O-acetyl-11-keto-beta-boswellic acid and their method of preparation are presented. The analogs may be used as anti-inflammatory and anti-cancer agents. The compounds inhibit 5-lipoxygenase enzyme and various cell lines related to inflammation as well as to cancer showing a significantly better efficacy when compared to the normal boswellic acids. The analogs are capable of controlling and treating various inflammatory diseases and cancers.

2 Claims, 3 Drawing Sheets

Figure-IA
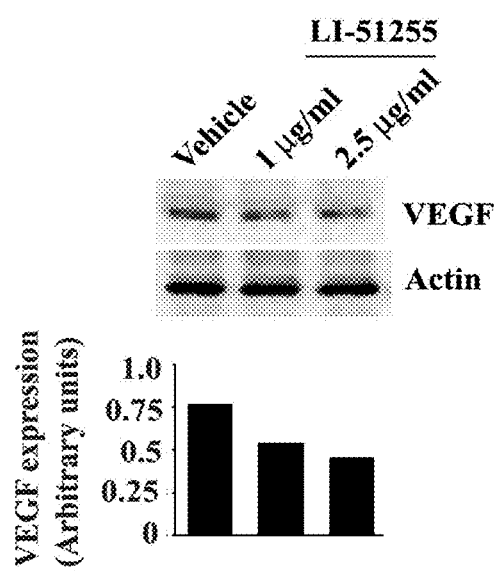
Figure IB
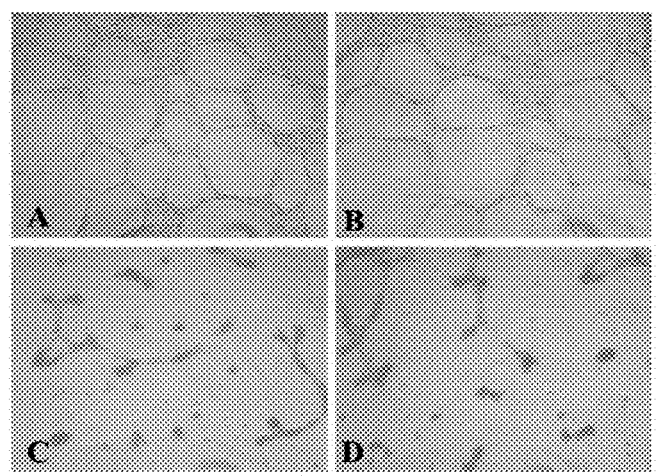

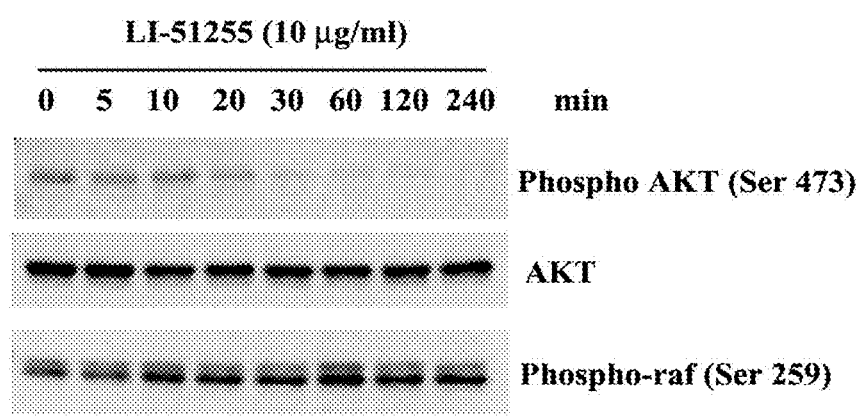
Figure-II

Figure-III
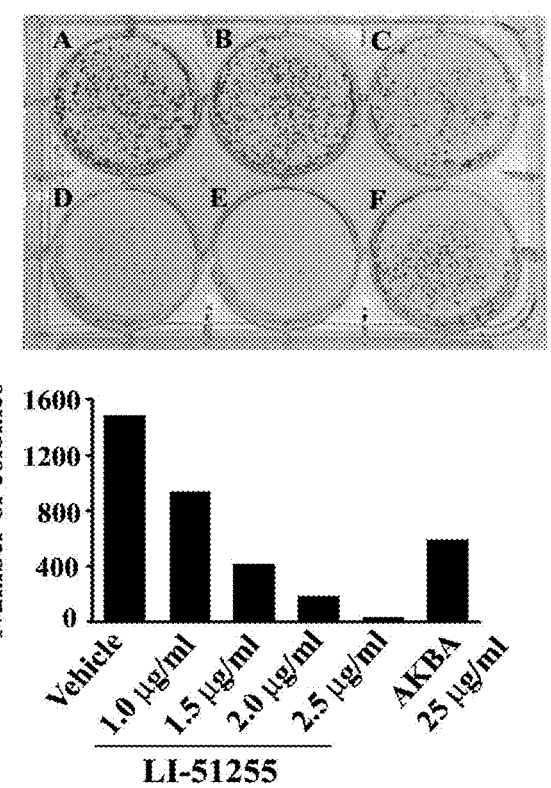

ANALOGS OF 3-O-ACETYL-11-KETO-BETA-BOSWELLIC ACID

RELATED APPLICATIONS

This application is a Continuation-In-Part of U.S. patent application Ser. No. 12/549,663, filed Aug. 28, 2009, which is a Division of U.S. patent application Ser. No. 10/540,257, filed Jun. 22, 2005, now U.S. Pat. No. 7,625,947, which is a national phase of International Application No. PCT/IN2004/000176, filed Jun. 18, 2004, all of which are herein incorporated by reference in their entirety.

DESCRIPTION OF FIGURES

FIG. IA: Representative Immunoblot shows LI-51255 [N-(3-O-Acetyl-11-ketoboswelloyl)-ethylenediamine (21)] down-regulates VEGF protein expression in HUVEC human endothelial cells. Bar graph shows normalized VEGF expression in respective treatments.

FIG. IB: LI-51255 [N-(3-O-Acetyl-11-ketoboswelloyl)-ethylenediamine (21)] inhibits capillary-like tube formation. Human umbilical vein endothelial cells (HUVECs) were laid on Cultrex coated plates in presence of either LI-51255 (1, 2.5 and 5 µg/ml at panel B, C and D respectively) or 0.5% DMSO as vehicle (panel A) and allowed to form endothelial capillary tubes for 16 h at 37° C.

FIG. II: LI-51255 [N-(3-O-Acetyl-11-ketoboswelloyl)-ethylenediamine (21)] inhibits AKT pathway in MDA-MB-231 cells. Western Immunoblot images represent time dependent down regulation of phosphorylated AKT (ser 473) protein expression and up-regulation of phospho-raf (ser 259) expression in MDA-MB-231 cells by LI-51255, whereas, the AKT protein expression remains the same during the period of incubation.

FIG. III. Photograph represents images showing inhibition of MDA-MB-231 colony formation in presence of LI-51255 [N-(3-O-Acetyl-11-ketoboswelloyl)-ethylenediamine (21)] and AKBA in vitro. Equal number of MDA-MB-231 cells was treated with either 0.5% DMSO (A), or different concentrations of LI-51255 (1.0, 1.5, 2.0, 2.5 µg/ml in B, C, D and E, respectively) or with 25 µg/ml AKBA (F). Bar diagram represents the average number of colonies in each treatment well as indicated.

DETAILED DESCRIPTION

Inflammation is a complex process that occurs in response to noxious stimuli, trauma or infection. The response is modulated by inflammatory mediators such as kinins, cytokines, eicosanoids and adhesion molecules like ICAM and VCAM. Even though inflammation is critical for human survival to counter microbial onslaughts and unforeseen and accidental injuries, it is the Root cause of the major chronic diseases. Inflammation can be controlled effectively by inhibiting the formation of inflammatory mediators like eicosanoids such as prostaglandins and leukotrienes. The formation of eicosanoids such as prostaglandins and leukotrienes from arachidonic acid released from the cell membranes is mediated by cyclooxygenase (COX) and lipooxygenase (LOX) respectively. The search for inhibitors of COX and LOX enzymes for suppressing the formation inflammatory mediators is the basis for the development of new anti-inflammatory agents. However, recent studies revealed that COX inhibitors causes side effects, especially those leading to cardiovascular problems. The alternative pathway mediated by 5-lipoxygenase (5-LOX) has thus become an important target for the development of anti-inflammatory drugs.

The applicants have thus prepared a number of analogs of natural products and found that the analogs of 3-O-acetyl-11-keto-β-boswellic acid (AKBA) show very potent inhibitory activity against 5-lipoxygenase (5-LOX). The analogs represented by the structural formulae 1 to 58 were prepared and tested for their potential uses as anti-inflammatory and anti-tumor or anti-cancer agents.

For the sake of understanding the description, the structure formula for each analog is assigned with an analog number that is typed in bold numbers and the structure formula or its analog number are used interchangeably in description as well as in claims, where ever applicable. Also in the methods of preparation, 'RM' indicates 'Reaction mixture'; 'RT' indicates 'Room Temperature'.

The analogs 1 to 27 described below are already disclosed in our earlier application Ser. No. 10/540,257 which is granted on Dec. 1, 2009 under grant number U.S. Pat. No. 7,625,947, where re incorporated herein by reference.

The analogs described and claimed in earlier application are represented by the general formula I:

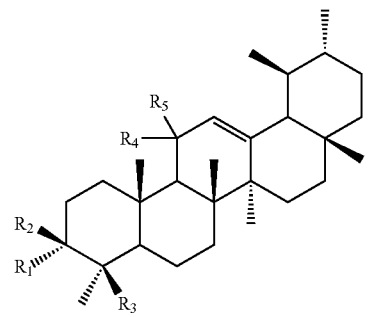

Where in $R_1$, $R_2$, $R_3$, $R_4$ and $R_5$ are as indicated below in each of said analogs:

1. $R_1$=OCHO, $R_2$=H, $R_3$=COOH, $R_4$ & $R_5$=O;
2. $R_1$=OCOCH$_2$Cl, $R_2$=H, $R_3$=COOH, $R_4$ & $R_5$=O;
3. $R_1$=5'-O-methylgalloyloxy, $R_2$=H, $R_3$=COOH, $R_4$ & $R_5$=O;
4. $R_1$=OCOCH$_2$CH$_2$COOH, $R_2$=H, $R_3$=COOH, $R_4$ & $R_5$=O;
5. $R_1$=8',9'-Dihydro-4'-hydroxycinnamoyloxy, $R_2$=H, $R_3$=COOH, $R_4$ & $R_5$=O;
6. $R_1$=4'-Hydroxycinnamoyloxy, $R_2$=H, $R_3$=COOH, $R_4$ & $R_5$=O;
7. $R_1$=3',4'-Dimethoxycinnamoyloxy, $R_2$=H, $R_3$=COOH, $R_4$ & $R_5$=O;
8. $R_1$=3',4'-Dihydroxy-5'-methoxycinnamoyloxy, $R_2$=H, $R_3$=COOH, $R_4$ & $R_5$=O;
9. $R_1$=OCOCH$_2$NH(tert-BOC), $R_2$=H, $R_3$=COOCH$_3$, $R_4$ & $R_5$=O;
10. $R_1$=OCOCH$_2$NH$_2$HCl, $R_2$=H, $R_3$=COOH, $R_4$ & $R_5$=O;
11. $R_1$=OCOCH(CH$_3$)NH$_2$HCl, $R_2$=H, $R_3$=COOH, $R_4$ & $R_5$=O;
12. $R_1$=H, $R_2$=OH, $R_3$=COOCH$_3$, $R_4$ & $R_5$=O;
13. $R_1$=H, $R_2$=Br, $R_3$=COOCH$_3$, $R_4$ & $R_5$=O;
14. $R_1$=CN, $R_2$=H, $R_3$=COOCH$_3$, $R_4$ & $R_5$=O;
15. $R_1$=SH, $R_2$=H, $R_3$=COOCH$_3$, $R_4$ & $R_5$=O;
16. $R_1$ & $R_2$=N(OH), $R_3$=COOCH$_3$, $R_4$ & $R_5$=O;
17. $R_1$ & $R_2$=H & OCOCH$_3$ $R_3$=H, $R_4$ & $R_5$=O;
18. $R_1$=OCOCH$_3$, $R_2$=H $R_3$=COOCH$_2$CH$_2$N(CH$_3$)$_2$, $R_4$ & $R_5$=O;

19. $R_1$=OCOCH$_3$, $R_2$=H $R_3$=CONH$_2$, $R_4$& $R_5$=O;
20. $R_1$=OCOCH$_3$, $R_2$=H, $R_3$—CONHNH$_2$, $R_4$& $R_5$=O;
21. $R_1$=OCOCH$_3$, $R_2$=H, $R_3$=CONHCH$_2$CH$_2$NH$_2$, $R_4$& $R_5$=O;
22. $R_1$=OCOCH$_3$, $R_2$=H, $R_3$=CONHCH$_2$CH$_2$OH, $R_4$& $R_5$=O;
23. $R_1$=OCOCH$_3$, $R_2$=H, $R_3$=CON(CH$_2$CH$_2$)$_2$NH, $R_4$& $R_5$=O;
24. $R_1$=OCOCH$_3$, $R_2$=H $R_3$=NCO, $R_4$& $R_5$=O;
25. $R_1$=OCOCH$_3$, $R_2$=H $R_3$=NH$_2$, R4 & $R_5$=O;
26. $R_1$=OCOCH$_3$, $R_2$=H $R_3$=CN, $R_4$& $R_5$—O;
27. $R_1$=OH, $R_2$=H $R_3$=COOH, $R_4$& $R_5$—OH & H;

The preferred compounds are:
1. 3-O-Formyl-11-keto[beta]-boswellic acid,
2. 3-O-(Chloroacetyl)-11-keto-[beta]-boswellic acid,
3. 3-O-(5'-O-methylgalloyl)-11-keto-[beta]-boswellic acid,
4. 3-O-Succinyl-11-keto[beta]-boswellic acid,
5. 3-O-[8',9'-Dihydro-4'-hydroxycinnamoyl]-11-keto-[beta]-boswellic acid,
6. 3-O-[4'-Hydroxycinnamoyl]-11-keto-[beta]-boswellic acid,
7. 3-O-(3',4'-dimethoxycinnamoyl)-11-keto[beta]-boswellic acid,
8. 3-O-(3',4'-Dihydroxy-5'-methoxycinnamoyl)-11-keto-[beta]-boswellic acid,
9. Methyl 3-O—(N-Boc-glycyl)-11-keto-[beta]-boswellate,
10. 3-O-Glycyl-11-keto-[beta]-boswellic acid hydrochloride,
11. 3-O-Alanyl-11-keto[beta]-boswellic acid hydrochloride,
12. Methyl 3-hydroxy-11-ketours-12-en-24-oate,
13. Methyl 3-bromo-11-ketours-12-en-24-oate,
14. Methyl 3[alpha]-cyano-11-ketours-12-en-24-oate,
15. Methyl 3[alpha]-thiohydroxy-11-ketours-12-en-24-oate,
16. Methyl 3-oximino-11-ketours-12-en-24-oate,
17. 3-Acetoxy-11-keto-24-norurs-12-ene,
18. (2'-N,N-Dimethylaminoethyl) 3-O-acetyl-11-keto-[beta]-boswellate,
19. 3-O-Acetyl-11-keto-[beta]-boswellic acid amide,
20. N-(3-O-Acetyl-11-keto-[beta]-boswelloyl)-hydrazide,
21. N-(3-O-Acetyl-11-keto-[beta]-boswelloyl)-ethylenediamine,
22. N-(3-O-Acetyl-11-keto[beta]-boswelloyl)-2-aminoethanol,
23. N-(3-O-Acetyl-11-keto-[beta]-boswelloyl)-piperzine,
24. 3-Acetoxy-11-keto-24-norurs-12-en-4-isocyanate,
25. 3-Acetoxy-4-amino-11-keto-24-norurs-12-ene,
26. 3-Acetoxy-4-cyano-11-keto-24-norurs-12-ene,
27. 11-Hydroxy-[beta]-boswellic acid.

Their structural formulae are given below:

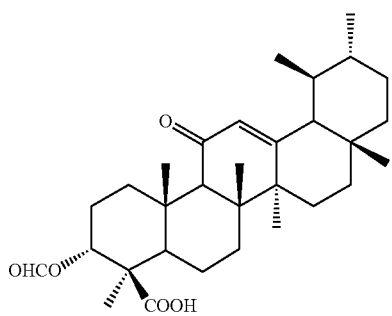

1

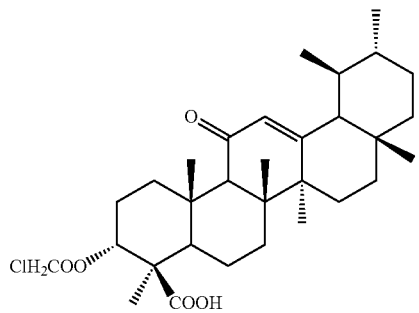

2

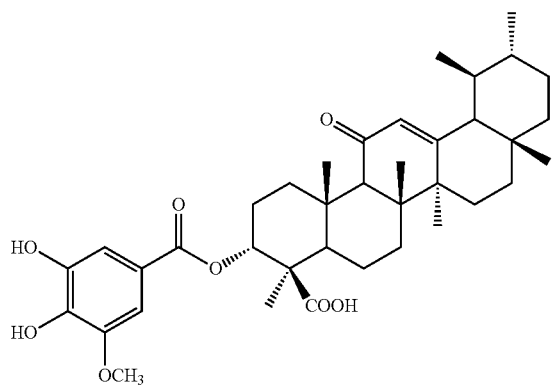

3

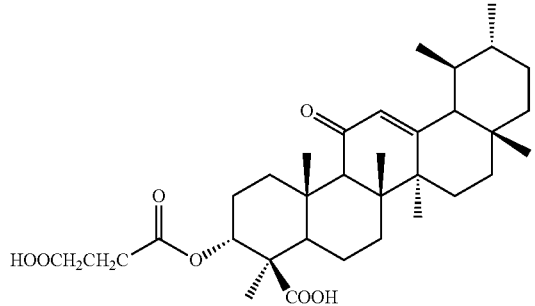

4

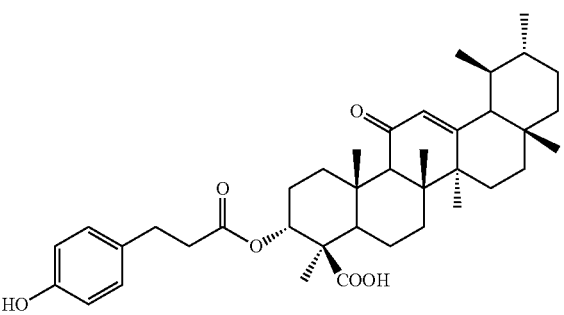

5

5
-continued
6
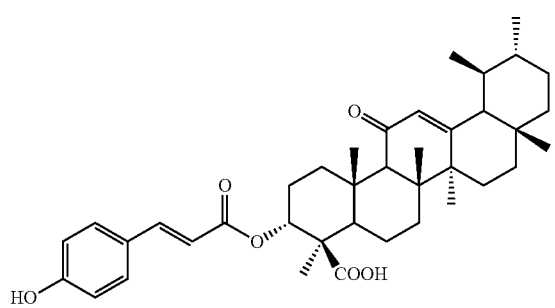
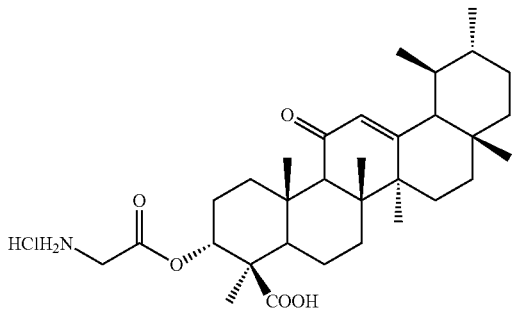
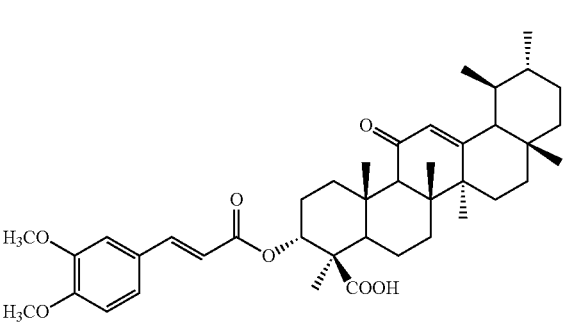
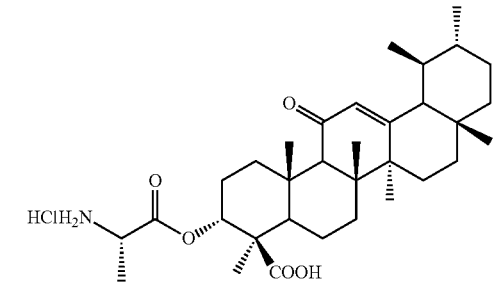
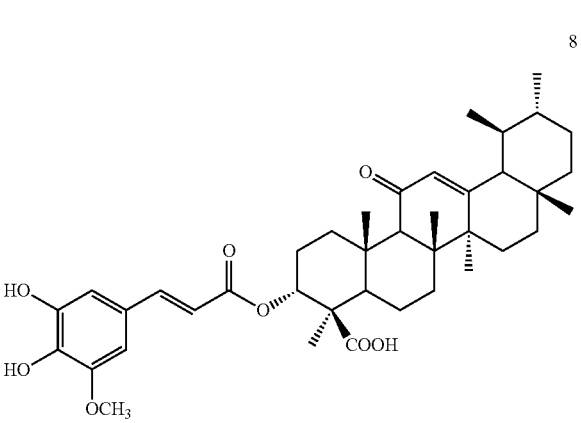
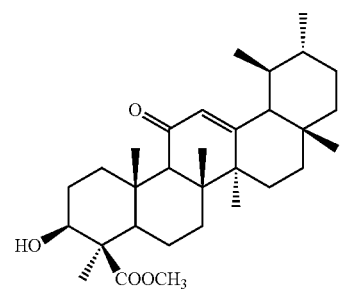
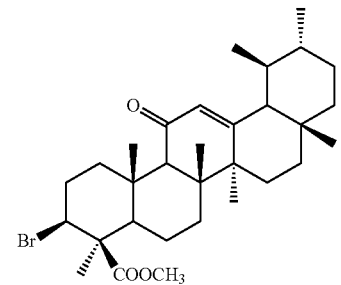
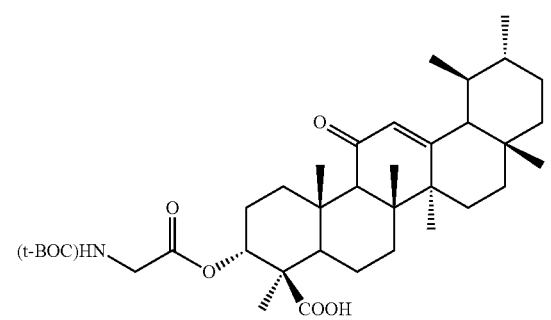
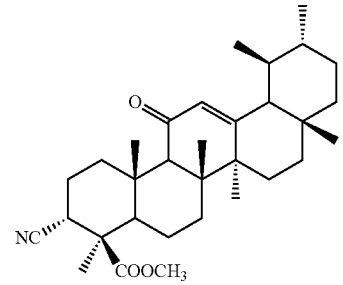

-continued
15
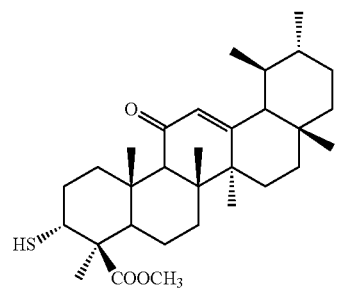
16
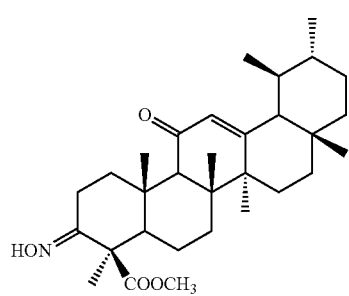
17
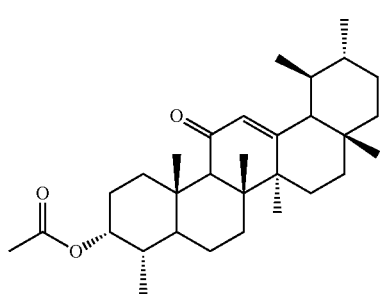
18
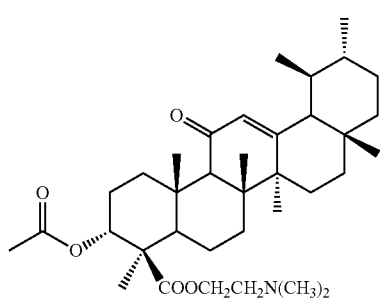
19
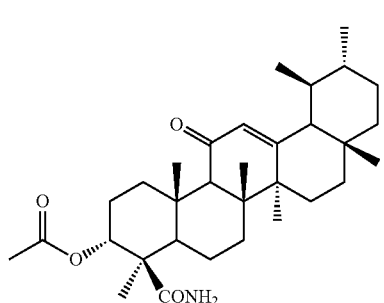
-continued
20
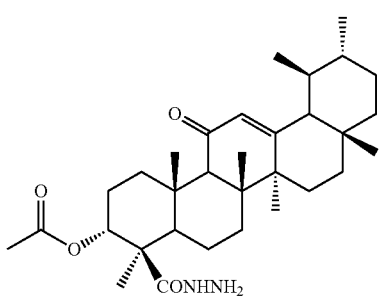
21
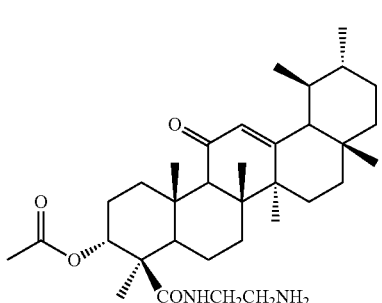
22
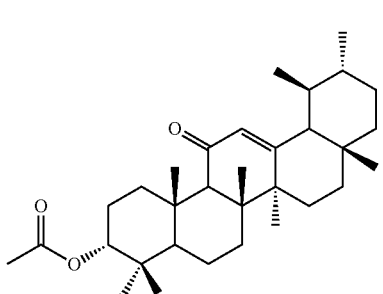
23
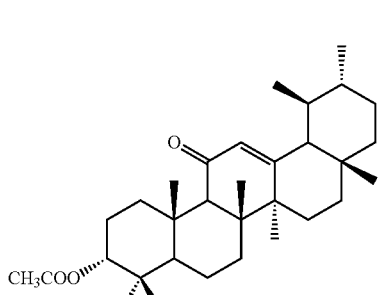
24
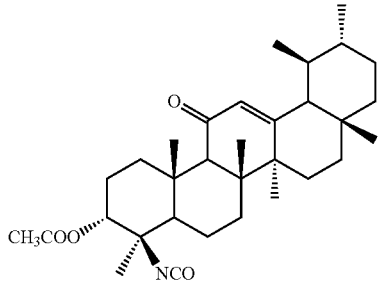

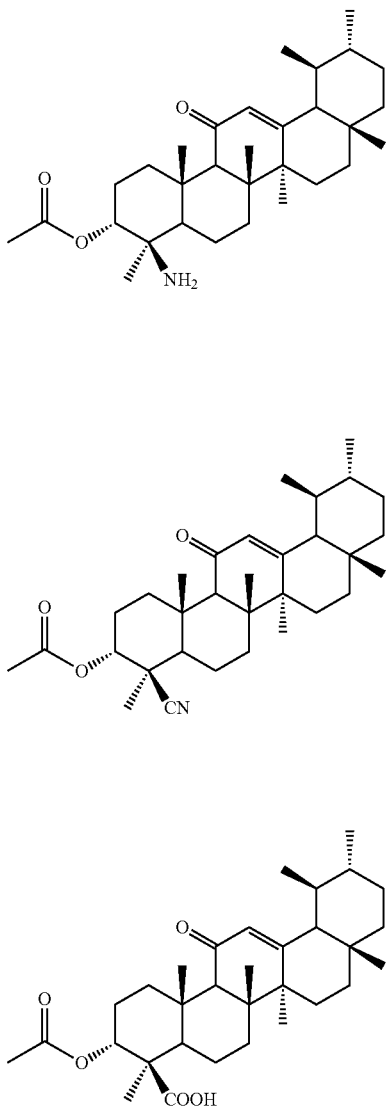

The analogs 28 to 63 represented by the same structural formula I have now been prepared and the structural details are summarized below.

One embodiment relates to novel AKBA analogs of Formula-I given below:

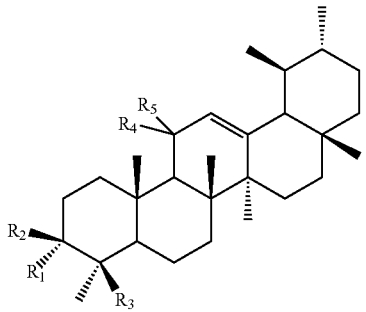

Formula-I

Wherein $R_1$, $R_2$, $R_3$, $R_4$ and $R_5$ are as indicated below in each of the said analogs:

28. $R_1$=OCOCH$_3$, $R_2$=H, $R_3$=CON(CH(CH$_3$)$_2$)$_2$, $R_4$ & $R_5$=O;
29. $R_1$=OCOCH$_3$, $R_2$=H, $R_3$=CONHCH$_2$CH$_2$CH$_2$CH$_3$, $R_4$ & $R_5$=O;
30. $R_1$=OCOCH$_3$, $R_2$=H, $R_3$=CONHCH(CH$_3$)$_2$, $R_4$ & $R_5$=O;
31. $R_1$=OCOCH$_3$, $R_2$=H, $R_3$=CON(CH$_3$)$_2$, $R_4$ & $R_5$=O;
32. $R_1$=OCOCH$_3$, $R_2$=H, $R_3$=CONHCH$_2$COOCH$_3$, $R_4$ & $R_5$=O;
33. $R_1$=OCOCH$_3$, $R_2$=H, $R_3$=CONHCH$_2$(CH$_2$)$_4$CH$_2$NH$_2$, $R_4$ & $R_5$=O;
34. $R_1$=OCOCH$_3$, $R_2$=H, $R_3$=CONHCH$_2$(CH$_2$)$_2$CH$_2$NH$_2$, $R_4$ & $R_5$=O;
35. $R_1$=OCOCH$_3$, $R_2$=H, $R_3$=CONHCH$_2$(CH$_2$)$_5$CH$_2$NH$_2$, $R_4$ & $R_5$=O;
36. $R_1$=OH, $R_2$=H, $R_3$=CON(CH$_2$CH$_2$)$_2$O, $R_4$ & $R_5$=O;
37. $R_1$=OCOCH$_3$, $R_2$=H, $R_3$=CON(CH$_2$CH$_2$)$_2$O, $R_4$ & $R_5$=O;
38. $R_1$=OH, $R_2$=H, $R_3$=CON(CH$_2$CH$_2$)$_2$NCH$_2$CH$_2$OH, $R_4$ & $R_5$=O;
39. $R_1$=OOCH$_3$, $R_2$=H, $R_3$=CON(CH$_2$CH$_2$)$_2$NCH$_2$CH$_2$OH, $R_4$ & $R_5$=O;
40. $R_1$=OCOCH$_3$, $R_2$=H, $R_3$=Imidazole-1-carbonyl, $R_4$ & $R_5$=O;
41. $R_1$=OCOCH$_3$, $R_2$=H, $R_3$=2-Aminoindane-N-carbonyl, $R_4$ & $R_5$=O;
42. $R_1$=OCOCH$_3$, $R_2$=H, $R_3$=CONHC$_6$H$_5$, $R_4$ & $R_5$=O;
43. $R_1$=OCOCH$_3$, $R_2$=H, $R_3$=CONHCH$_3$, $R_4$ & $R_5$=O;
44. $R_1$=OCOCH$_3$, $R_2$=H, $R_3$=CONH(2-C$_6$H$_4$Br), $R_4$ & $R_5$=O;
45. $R_1$=OCOCH$_3$, $R_2$=H, $R_3$=CON(CH$_3$)CH$_2$CH$_2$OH, $R_4$ & $R_5$=O;
46. $R_1$=OCOCH$_3$, $R_2$=H, $R_3$=CONH(p-C$_6$H$_4$OH), $R_4$ & $R_5$=O;
47. $R_1$=OCOCH$_3$, $R_2$=H, $R_3$=CONHNHC$_6$H$_5$, $R_4$ & $R_5$=O;
48. $R_1$=OCOCH$_3$, $R_2$=H, $R_3$=CONHCH$_2$CH$_2$NHCHO, $R_4$ & $R_5$=O;
49. $R_1$=OCOCH$_3$, $R_2$=H, $R_3$=CONHCH$_2$CH$_2$N(CH$_2$CH$_2$OH)$_2$., $R_4$ & $R_5$=O;
50. $R_1$=OCOCH$_3$, $R_2$=H, $R_3$=CONHCH$_2$CH$_2$NHCOCHCH(3,4-C$_6$H$_3$O$_2$CH$_2$), $R_4$ & $R_5$=O;
51. $R_1$=OCOCH$_3$, $R_2$=H, $R_3$=CONHCH$_2$CH$_2$NH$_2$, $R_4$ & $R_5$=H;
52. $R_1$=OCOCH$_3$, $R_2$=H, $R_3$=CONH$_2$, $R_4$ & $R_5$=H;
53. $R_1$=OCOCH$_3$, $R_2$=H, $R_3$=CONHCH$_2$CH$_2$OH, $R_4$ & $R_5$=H;
54. $R_1$=OCOCH$_3$, $R_2$=H, $R_3$=CON(CH$_2$CH$_2$)$_2$NH, $R_4$ & $R_5$=H;
55. $R_1$=OCOCH$_3$, $R_2$=H, $R_3$=CONHCH$_2$CH$_2$NHCH$_3$, $R_4$ & $R_5$=O;
56. $R_1$=OCOCH$_3$, $R_2$=H, $R_3$=CONHCH(COOCH$_3$)CH$_2$CH$_2$COOCH$_3$, $R_4$ & $R_5$=O;
57. $R_1$ & $R_2$=NOH, $R_3$=CONH$_2$, $R_4$ & $R_5$=O;
58. $R_1$ & $R_2$=NHCOCH$_3$, $R_3$=COOCH$_3$, $R_4$ & $R_5$=O;

The structural formulae for the analogs 28 to 58 disclosed below:
28
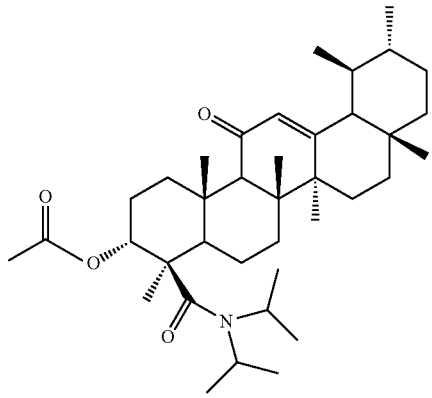
29
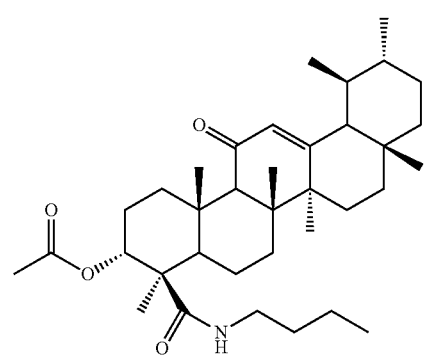
30
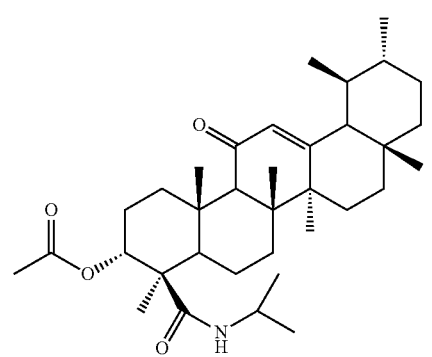
31
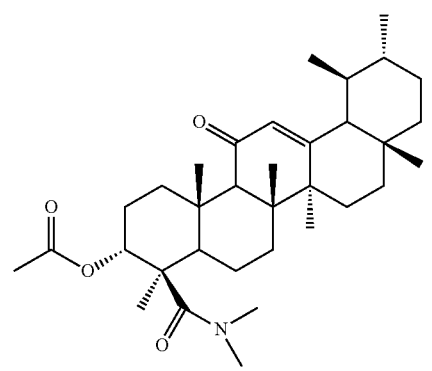
32
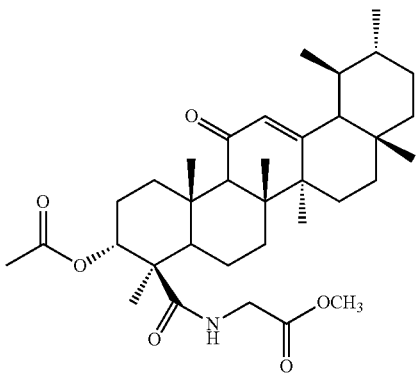
33
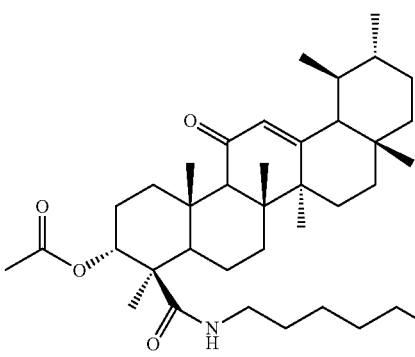
34
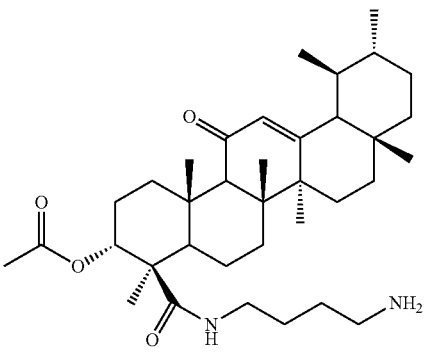
35
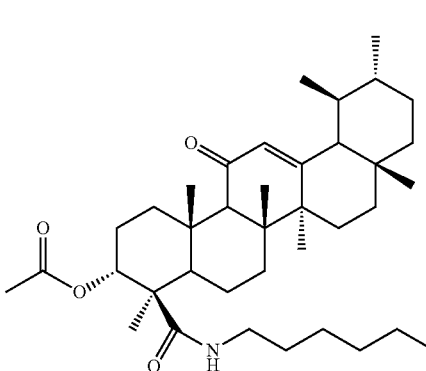

36
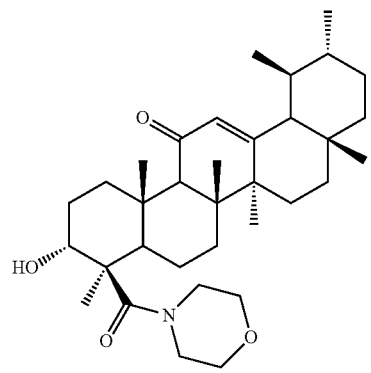
37
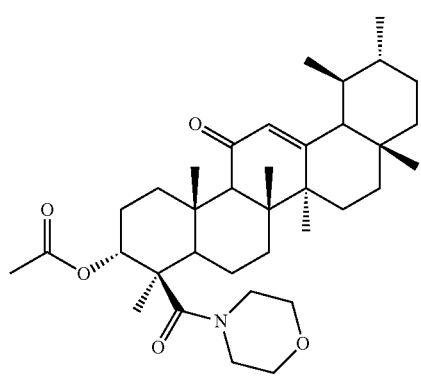
38
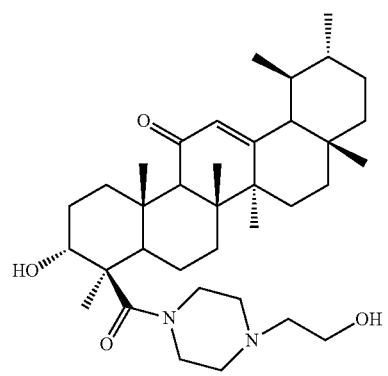
39
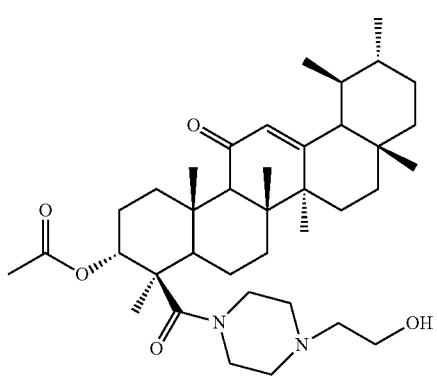
40
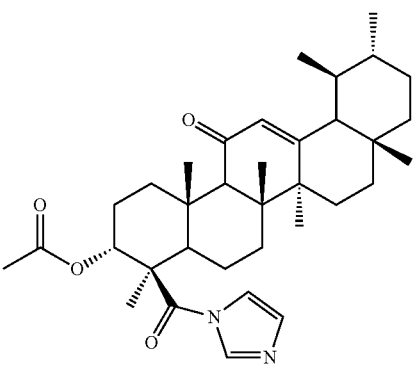
41
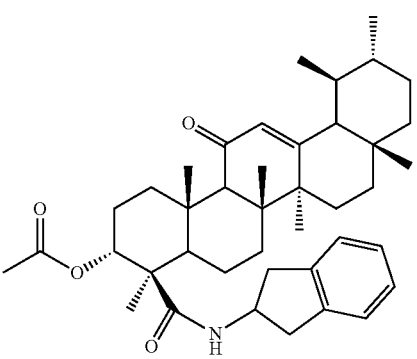
42
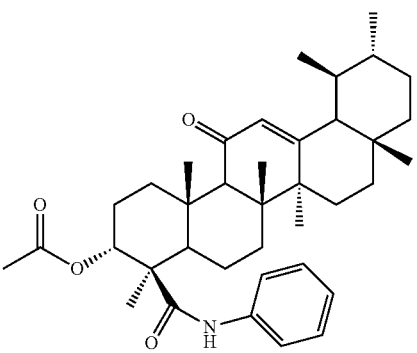
43
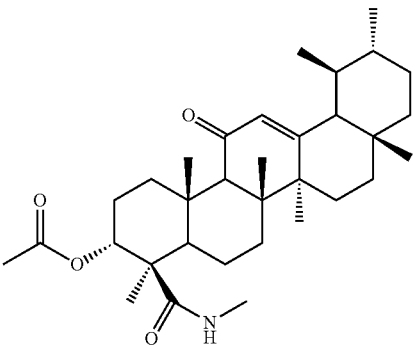

44
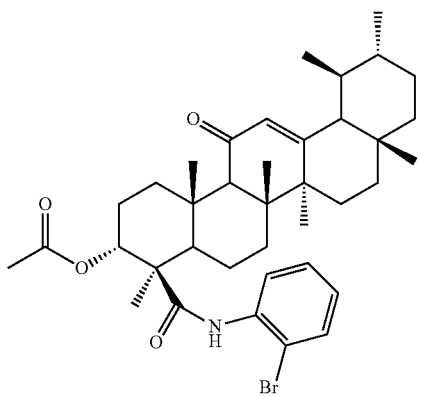
45
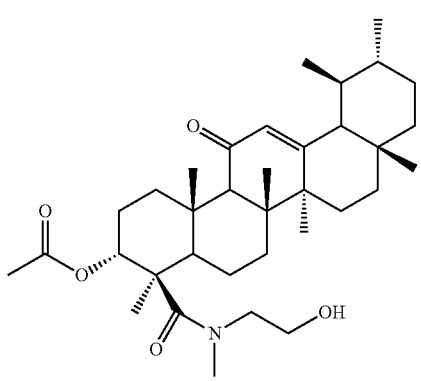
46
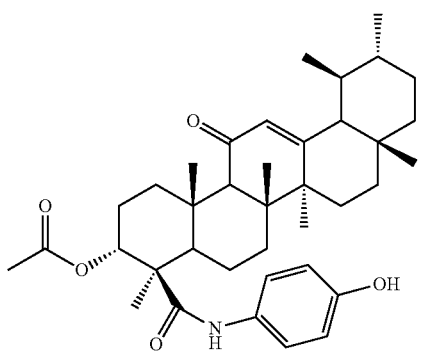
47
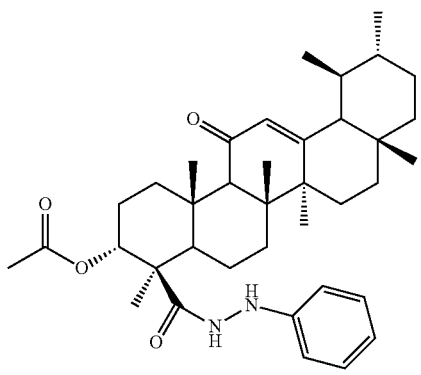
48
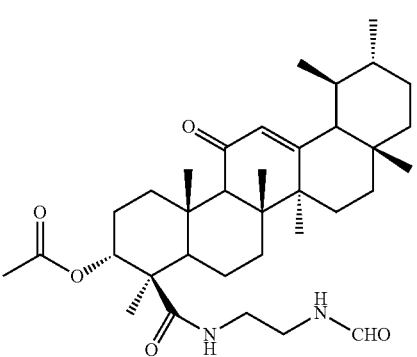
49
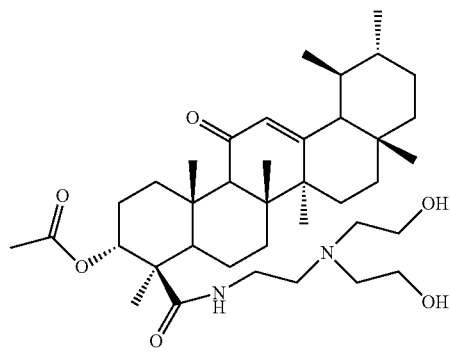
50
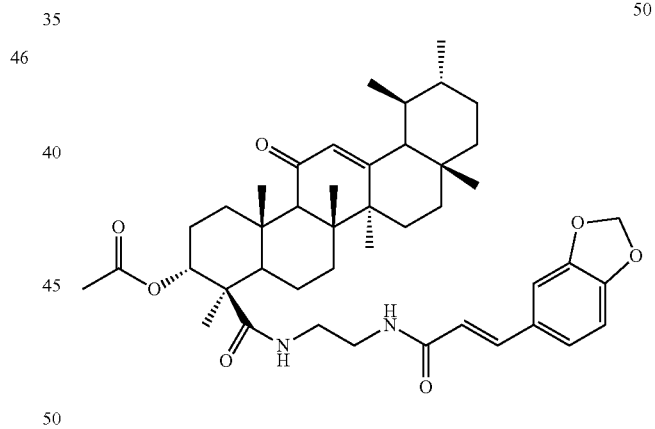
51
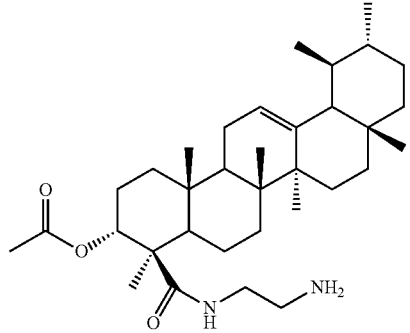

52
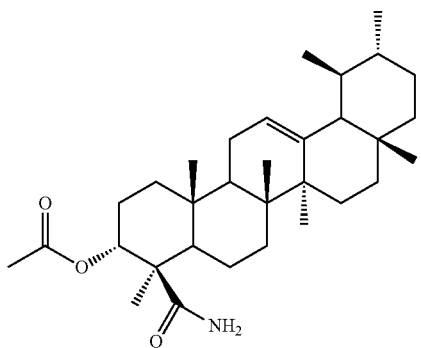
53
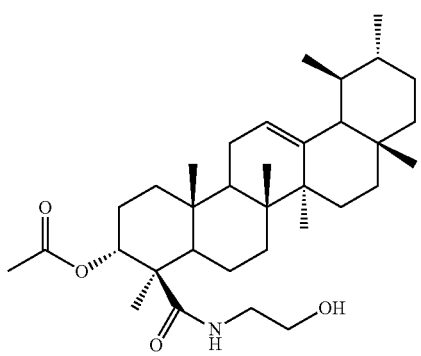
54
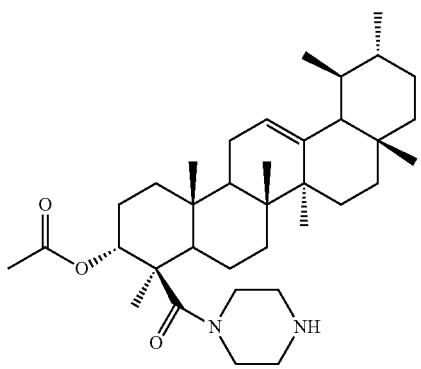
55
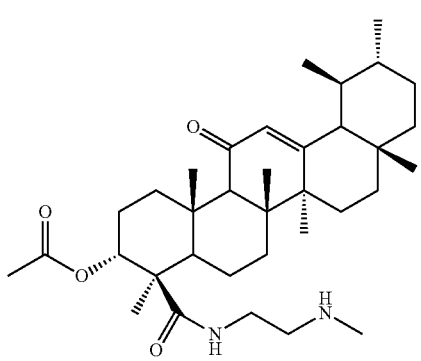
56
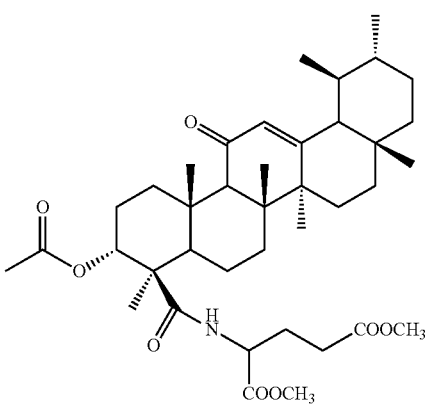
57
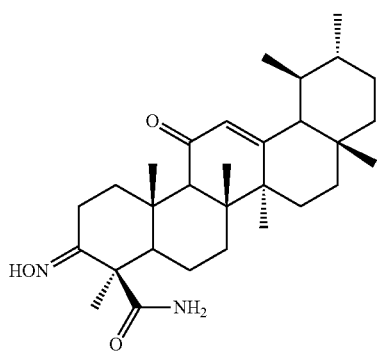
58
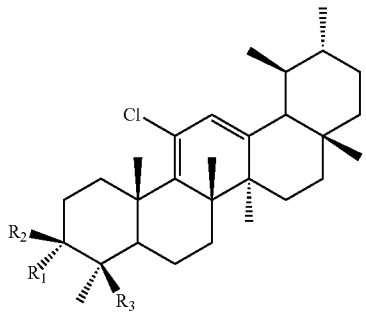
One embodiment further discloses novel AKBA analogs of Formula-II given below:
Formula II
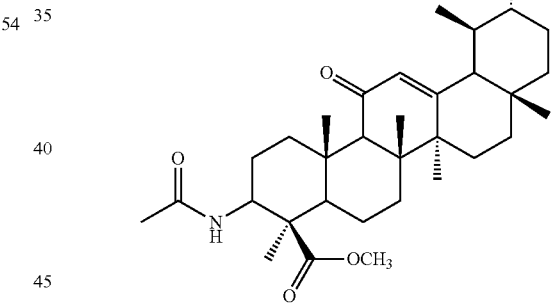

Wherein $R_1$, $R_2$ and $R_3$ are as indicated below in each of said analogs:

59. $R_1$=OH, $R_2$=H, $R_3$=COOH;
60. $R_1$=OCOCH$_3$, $R_2$=H, $R_3$=COOH;
61. $R_1$=OCOCH$_3$, $R_2$=H, $R_3$=CONHCH$_2$CH$_2$NH$_2$;
62. $R_1$=OCOCH$_3$, $R_2$=H, $R_3$=CONHNH$_2$;
63. $R_1$=OCOCH$_3$, $R_2$=H, $R_3$=CON(CH$_2$CH$_2$)$_2$NH;

The structural formulae for the analogs 59 to 63 are given below

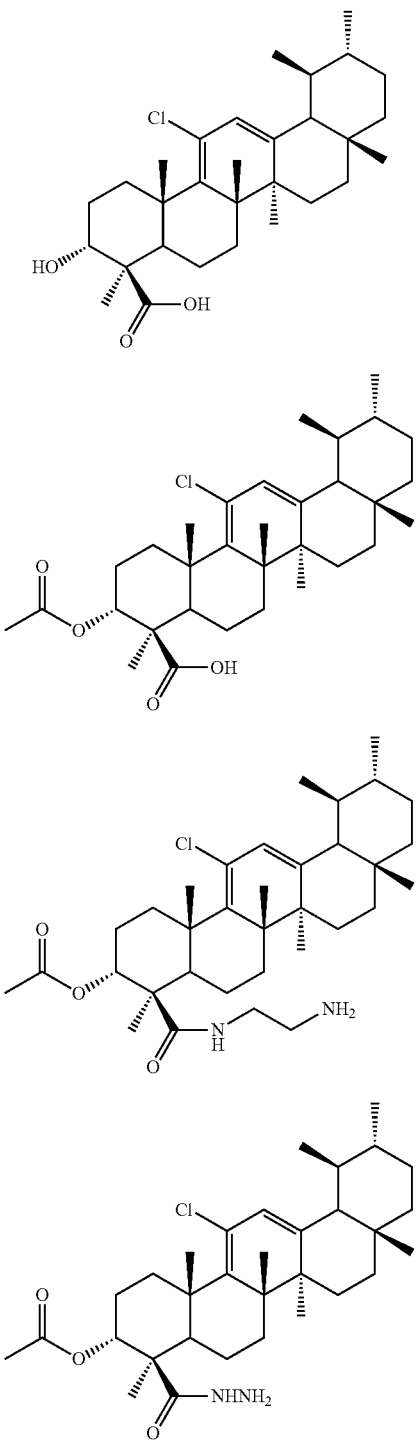

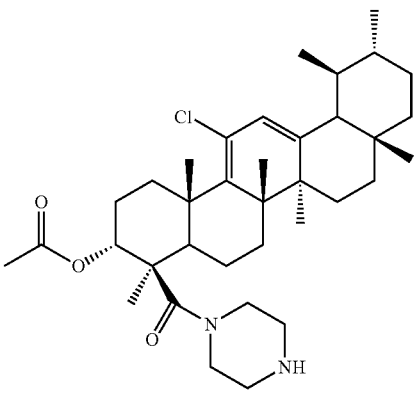

The 5-lipoxygenase activity of AKBA analogs 1 to 28 were already disclosed in our earlier application Ser. No. 10/540,257, which is granted under number U.S. Pat. No. 7,625,947 on Dec. 1, 2009. The details are incorporated herein by reference. The 5-lipoxygenase inhibitory activity of the analogs 28 to 63 are summarized in table 1. The analogs showed very potent inhibition against 5-lipoxygenase enzyme, manifesting their potential as an anti-inflammatory agents. The efficacy shown by the analogs in vitro was further substantiated by an in vivo Freund's adjuvant-induced arthritis study in Wistar Albino rats using the analogs 10 and 23 as representative examples. The efficacy shown by the analog 23 at 10 mg/kg dose (16.3%) was comparable to that shown by the positive control prednisolone (16.8%). The analog 10 showed moderate inhibition of paw edema (12%).

Chronic inflammation predisposes to some forms of human cancers. A molecular link has recently been established between inflammation and cancer by scientists at the University of California, San Diego, School of Medicine (Greten F R, et. al. Cell 2004; 118(3): 285-96). Experimental and epidemiological studies demonstrated that many non steroidal anti-inflammatory drugs (NSAIDS) are effective in prevention of human cancers. The leukotrienes (LTS) and hydroxyl eicosa tetetraenoic acid (HETEs), the major metabolic products of 5-lipooxygenase pathway, exert profound biological effects in the development and progression of human cancers. The LOX inhibitors are thus potential targets not only for treatment of inflammatory diseases but also for chemoprevention, treatment and control of cancers. The natural boswellic acids inhibited leukemia and melanoma cell lines in vitro 11 and they are also known to be dual inhibitors of human Topoisomerases-I and II α.12 The authors thus attempted to evaluate the anti-proliferative properties of the new analogs developed as part of this study.

The Brine shrimp lethality of the analogs was evaluated as it has been shown to be corroborative with the cytotoxicity data determined for 9 KB and 9PS cells (McLaughlin et. al., 1992 and 1998). The Brine shrimp lethality was evaluated for the analogs 1 to 28 and compared the activities with those of AKBA and a standard compound podophyllotoxin. The data was summarized already disclosed in our earlier application Ser. No. 10/540,257 which is granted under U.S. Pat. No. 7,625,947 which is incorporated herein by reference. The magnitude of Brine shrimp lethality obtained for the analogs has significant correlation with 5-LOX inhibitory activity. The piperazine amide of AKBA (23), with an IC50 of 0.88 μM, is more potent of all the analogs and its activity is significantly higher comparable to that of the standard drug podophyllotoxin, whose IC50 is 3 μM. All the other amides and the amine compound (25), which were found to be very potent against 5-LOX also showed potent inhibitory capabilities against brine shrimp.

Encouraged by the above finding, the authors subjected a group of selected AKBA analogs to cytotoxicity evaluation against several human tumor cell lines such as Jurkat (human T-cell lymphoblast-like cancer cell line), PC-3M (human prostate carcinoma cell line), DU 145 (human prostate cancer cell line), HepG2 (human hepatocellular liver carcinoma cell line), MCF-7 (human breast adenocarcinoma cell line), MDA-MB-231 (breast cancer cell line), A375 (human melanoma cell line), A2058 (human melanoma cell line), B16 (mouse melanoma cell line), A549 (human lung adenocarcinoma epithelial cell line) and HT-29 (human colon adenocarcinoma cell line). The 3-O-monomethylgallyl derivative (3), hydrazine amide (20), piperazine amide (23) and the amine (25) were significantly more potent against PC3M, where as ammonia amide (19) and ketoxime (16) were highly potent selectively against leukemia cells. The analog, N-(3-O-acetyl-11-keto boswelloyl) ethylene diamine (21), which is herein after also referred to as LI51255, showed potent in vitro anti-cancer activities broadly against several tumor cell lines as summarized below. More importantly LI-51255 also potently inhibited two breast tumor cell lines MCF-7 and MDA-MB-231 with IC50 values of 12.98 and 3.45 µg/mL respectively.

| In vitro antitumor activity of analog 21 | |
|---|---|
| Tumor Cell line | Inhibition of cell proliferation by analog 21(IC50 µg/ml) |
| A375 | 3.53 |
| A2058 | 3.59 |
| DU145 | 4.24 |
| B16 | 4.35 |
| SKBR3 | 5.3 |
| A549 | 6.83 |
| HT-29 | 8.87 |

The mechanistic aspects of the analog LI51255 [N-(3-O-acetyl-11-ketoboswelloyl) ethylene diamine (21)] evaluated intensively. It strongly inhibited the expression of vascular endothelial growth factor (VEGF) indicating that LI-51255 suppresses angiogenesis in tumor cells (FIG. IA). This observation is further supported by dose dependent inhibition of human endothelial capillary formation in vitro by 21 (FIG. IB). This indicates that 21 can control the tumor growth by inhibiting or blocking blood circulation to tumor tissue. It was further demonstrated that 21 inhibits PI3K pathway by down regulating AKT phosphorylation in human metastatic breast tumor cells (FIG. II). This suggests that 21 can inhibit metastatic progression of tumors. In addition, 21 showed potent inhibition of clone formation in human breast cells in vitro (FIG. III). Further experimentation showed that 21 interrupts cell cycle progression at sub G1 phase in murine melanoma cells as summarized in table-4. The efficacy shown by LI-51255 in vitro was further confirmed in vivo by an animal experiment. The in vivo efficacy of LI-51255 was evaluated against melanoma growth in B16 F0 melanoma xenograft model of C57B6J mice. LI-51255 unexpectedly showed dose dependent inhibition of tumor growth (27.25% and 51.5% reduction in tumor burden respectively at 10 mg/kg and 20 mg/kg doses), and its efficacy was several fold better compared to the currently marketed melanoma drug Dacarbazine (DTIC), which showed 33.6% reduction at 75 mg/kg dose. The foregoing data substantiate the potential usefulness of 21 in the treatment of several cancers. The other analogs of AKBA also showed potent inhibition of several tumor cell lines as summarized in tables-2 and 3.

Compounds of the disclosed embodiments may be prepared by the following representative processes.

The compounds represented by 2 to 11 may be prepared by a coupling reaction between KBA or its ester with an appropriate acid counterpart using DCC (1,3-dicyclohexylcarbodiimide) and DMAP {4-(dimethylamino)pyridine} as coupling agent in a suitable solvent system. This may also be accomplished by converting the acid corresponding to the acyloxy unit to the acid chloride using $SOCl_2$ (thionyl chloride) and then treating the acid chloride with KBA or its methyl ester, in the presence of an organic base. The compounds represented by 12, 13, 14 and 15 may be prepared by displacing the 3αOH group in methyl ester of KBA by Br using $PBr_3$ (phosphorus tribromide) and then further displacing the Br group with appropriate nucleophilic agents, such as $SH^-$, $CN^-$ etc.

The amide compounds represented by 19, 20, 21, 22 and 23 may be prepared by treating the acid chloride of AKBA with an excess of amine component in a suitable solvent system. This reaction scheme is shown in the scheme II below. The isocyanate and amine compounds represented by the structures 24 and 25 respectively may be prepared by Hoffmann rearrangement of the amide 19. The intermediate isocyanate, 24 may be obtained by reducing the reaction time and working-up the reaction before completion. The cyano analog 26 was prepared by treating 3-O-acetyl-11-keto-β-boswellic acid amide (19) with thionyl chloride. 11-hydroxy-β-boswellic acid (27) was prepared subjecting 11-keto-β-boswellic acid to lithium aluminum hydride reduction.

The analogs 28 to 57 were prepared by a coupling reaction between appropriate boswellic acid and appropriate amine counterpart, followed by modification wherever desired. The analogs 59 and 60 are prepared by treating AKBA with phosphorous pentachloride. ($PCl_5$) to obtain analog 60. The hydrolysis of which under basic conditions yielded analog 59. The analogs 61 to 63 were prepared by treating the acid chloride of 60 with ethylenediamine, hydrazine and piperazine respectively.

A major embodiment relates to the novel structural analogs of 3-O-acetyl-11-keto-beta-boswellic acid (AKBA) of the formula I represented below:

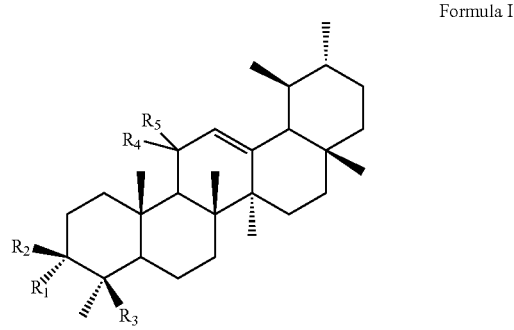

Formula I

Wherein $R_1$, $R_2$, $R_3$, $R_4$ and $R_5$ are as indicated below in each of the said analogs:
28. $R_1$=OCOCH$_3$, $R_2$=H, $R_3$=CON(CH(CH$_3$)$_2$)$_2$, $R_4$& $R_5$=O;
29. $R_1$=OCOCH$_3$, $R_2$=H, $R_3$=CONHCH$_2$CH$_2$CH$_2$CH$_3$, $R_4$& $R_5$=O;
30. $R_1$=OCOCH$_3$, $R_2$=H, $R_3$=CONHCH(CH$_3$)$_2$, $R_4$& $R_5$=O;
31. $R_1$=OCOCH$_3$, $R_2$=H, $R_3$=CON(CH$_3$)$_2$, $R_4$& $R_5$=O;

32. $R_1$=OCOCH$_3$, $R_2$=H, $R_3$=CONHCH$_2$COOCH$_3$, $R_4$ & $R_5$=O;
33. $R_1$=OCOCH$_3$, $R_2$=H, $R_3$=CONHCH$_2$(CH$_2$)$_4$CH$_2$NH$_2$, $R_4$ & $R_5$=O;
34. $R_1$=OCOCH$_3$, $R_2$=H, $R_3$=CONHCH$_2$(CH$_2$)$_2$CH$_2$NH$_2$, $R_4$ & $R_5$=O;
35. $R_1$=OCOCH$_3$, $R_2$=H, $R_3$=CONHCH$_2$(CH$_2$)$_5$CH$_2$NH$_2$, $R_4$ & $R_5$=O;
36. $R_1$=OH, $R_2$=H, $R_3$=CON(CH$_2$CH$_2$)$_2$O, $R_4$ & $R_5$=O;
37. $R_1$=OCOCH$_3$, $R_2$=H, $R_3$=CON(CH$_2$CH$_2$)$_2$O, $R_4$ & $R_5$=O;
38. $R_1$=OH, $R_2$=H, $R_3$=CON(CH$_2$CH$_2$)$_2$NCH$_2$CH$_2$OH, $R_4$ & $R_5$=O;
39. $R_1$=OOCH$_3$, $R_2$=H, $R_3$=CON(CH$_2$CH$_2$)$_2$NCH$_2$CH$_2$OH, $R_4$ & $R_5$=O;
40. $R_1$=OCOCH$_3$, $R_2$=H, $R_3$=Imidazole-1-carbonyl, $R_4$ & $R_5$=O;
41. $R_1$=OCOCH$_3$, $R_2$=H, $R_3$=2-Aminoindane-N-carbonyl, $R_4$ & $R_5$=O;
42. $R_1$=OCOCH$_3$, $R_2$=H, $R_3$=CONHC$_6$H$_5$, $R_4$ & $R_5$=O;
43. $R_1$=OCOCH$_3$, $R_2$=H, $R_3$=CONHCH$_3$, $R_4$ & $R_5$=O;
44. $R_1$=OCOCH$_3$, $R_2$=H, $R_3$=CONH(2-C$_6$H$_4$Br), $R_4$ & $R_5$=O;
45. $R_1$=OCOCH$_3$, $R_2$=H, $R_3$=CON(CH$_3$)CH$_2$CH$_2$OH, $R_4$ & $R_5$=O;
46. $R_1$=OCOCH$_3$, $R_2$=H, $R_3$=CONH(p-C$_6$H$_4$OH), $R_4$ & $R_5$=O;
47. $R_1$=OCOCH$_3$, $R_2$=H, $R_3$=CONHNHC$_6$H$_5$, $R_4$ & $R_5$=O;
48. $R_1$=OCOCH$_3$, $R_2$=H, $R_3$=CONHCH$_2$CH$_2$NHCHO, $R_4$ & $R_5$=O;
49. $R_1$=OCOCH$_3$, $R_2$=H, $R_3$=CONHCH$_2$CH$_2$N(CH$_2$CH$_2$OH)$_2$., $R_4$ & $R_5$=O;
50. $R_1$=OCOCH$_3$, $R_2$=H, $R_3$=CONHCH$_2$CH$_2$NHCOCHCH(3,4-C$_6$H$_3$O$_2$CH$_2$), $R_4$ & $R_5$=O;
51. $R_1$=OCOCH$_3$, $R_2$=H, $R_3$=CONHCH$_2$CH$_2$NH$_2$, $R_4$ & $R_5$=H;
52. $R_1$=OCOCH$_3$, $R_2$=H, $R_3$=CONH$_2$, $R_4$ & $R_5$=H;
53. $R_1$=OCOCH$_3$, $R_2$=H, $R_3$=CONHCH$_2$CH$_2$OH, $R_4$ & $R_5$=H;
54. $R_1$=OCOCH$_3$, $R_2$=H, $R_3$=CON(CH$_2$CH$_2$)$_2$NH, $R_4$ & $R_5$=H;
55. $R_1$=OCOCH$_3$, $R_2$=H, $R_3$=CONHCH$_2$CH$_2$NHCH$_3$, $R_4$ & $R_5$=O;
56. $R_1$=OCOCH$_3$, $R_2$=H, $R_3$=CONHCH(COOCH$_3$)CH$_2$CH$_2$COOCH$_3$, $R_4$ & $R_5$=O;
57. $R_1$ & $R_2$=NOH, $R_3$=CONH$_2$, $R_4$ & $R_5$=O;
58. $R_1$ & $R_2$=NHCOCH$_3$, $R_3$=COOCH$_3$, $R_4$ & $R_5$=O;

Another embodiment relates to the novel structural analogs of 3-O-acetyl-11-keto-beta-boswellic acid (AKBA) of the formula II represented below:

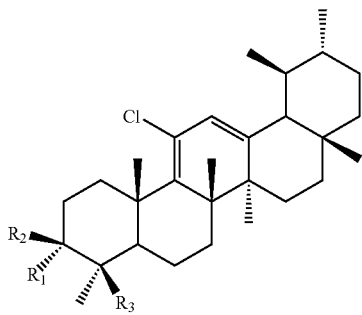

Formula II

Wherein $R_1$, $R_2$, $R_3$, $R_4$ and $R_5$ are as indicated below in each of the said analogs:
59. $R_1$=OH, $R_2$=H, $R_3$=COOH;
60. $R_1$=OCOCH$_3$, $R_2$=H, $R_3$=COOH;
61. $R_1$=OCOCH$_3$, $R_2$=H, $R_3$=CONHCH$_2$CH$_2$NH$_2$;
62. $R_1$=OCOCH$_3$, $R_2$=H, $R_3$=CONHNH$_2$;
63. $R_1$=OCOCH$_3$, $R_2$=H, $R_3$=CON(CH$_2$CH$_2$)$_2$NH;

Another embodiment relates to a method of treating inflammatory diseases comprising the step of administering at least one of the compound(s) selected from 1 to 63 described above or their compositions to a person in need thereof.

A preferred embodiment relates to the method of treating inflammatory disease, using above analogs, wherein the inflammatory disease is selected from the group consisting of arthritis, rheumatoid arthritis, osteoarthritis, inflammatory bowel disease, asthma, chronic obstructive pulmonary disease, allergic disorders and joint pain.

Another embodiment relates to a method of treating cancer diseases comprising the step of administering at least one of the compound(s) selected from 1 to 63 described above or their compositions to a person in need thereof.

Another embodiment relates to a method of treating cancer using at least one of the analog described above wherein the cancer is selected from the group including but not limited to breast cancer, liver cancer, spleen cancer, brain cancer, colon cancer, prostrate cancer, leukemia, melanoma, testicular cancer and lung cancer.

Another embodiment relates to a method of using the analogs and their compositions for treating cancer diseases including but not limited to prostrate cancer, Leukemia or blood cancer, hepatic cancer, breast cancer, brain cancer, colon cancer, melanoma, testicular cancer and lung cancer.

Another embodiment relates to a method of treating at least one inflammatory disease selected from including but not limited to arthritis, rheumatoid arthritis, osteoarthritis, inflammatory bowel disease, chronic obstructive pulmonary disease, allergic disorders and joint pain using boswellic acid analogs represented by the Formula II or their compositions.

Another embodiment relates to a method of treating at least one cancer disease selected from including but not limited to prostrate cancer, leukemia/blood cancer, hepatic cancer, breast cancer, colon, melanoma, testicular cancer, brain cancer and lung cancer using boswellic acid analogs represented by the Formula II or their compositions.

Another embodiment relates to a using at least one of the analog or their compositions disclosed in the specification as single ingredient as well as in composition in a therapeutically effective amount, preferably in a range of 0.0001% to 99.99% by weight.

Another embodiment relates to the formulation of analog(s) represented by Formula I and/or Formula II may be formulated in dry form, liquid form, food product, dietary supplement or any suitable form such as tablet, a capsule or a soft chew.

In another embodiment the analog(s) or composition(s) can be delivered in the form of controlled release tablets, using controlled release polymer-based coatings by the techniques including nanotechnology, microencapsulation, colloidal carrier systems and other drug delivery systems.

In another important embodiment the invention discloses the compositions containing at least one of the analogs (2 to 63) of the formulae I and II in combination with one or more pharmaceutically acceptable excipients, carriers and diluents, comprising glucose, fructose, sucrose, maltose, yellow dextrin, white dextrin, aerosil, microcrystalline cellulose, calcium stearate, magnesium stearate, sorbitol, stevioside, corn syrup, lactose, citric acid, tartaric acid, malic acid, succinic acid, lactic acid, L-ascorbic acid, dl-alpha-tocopherol, glycerin, propylene glycol, glycerin fatty ester, poly glycerin fatty ester, sucrose fatty ester, sorbitan fatty ester, propylene glycol fatty ester, acacia, carrageenan, casein, gelatin, pectin, agar, vitamin B group, nicotinamide, calcium pantothenate, amino acids, calcium salts, pigments, flavors, preservatives, distilled water, saline, aqueous glucose solution, alcohol, propylene glycol and polyethylene glycol, various animal and vegetable oils, white soft paraffin, paraffin and wax.

Those of ordinary skill in the art will appreciate that changes could be made to the embodiments described above without departing from the broad inventive concept thereof. It is understood, therefore, that this invention is not limited to the particular embodiments or examples disclosed, but is intended to cover modifications within the objectives and scope of the present invention as defined in the specification.

Compounds of this embodiment may be prepared by the following process.

EXAMPLES

Scheme I

Formula-I Analogs Preparation

Example 1

Preparation of Diisopropylamine amide of 3-O-acetyl-11-keto-β-boswellic acid (28)

A mixture of 3-O-acetyl-11-keto-β-boswellic acid (500 mg, 0.97 mmoles), 0.5 mL of thionyl chloride ($SOCl_2$) was taken in a round bottom flask (RB). Then reaction mixture (RM) was heated at 90° C. for 1 hour. Then RM was dried under high vacuum. Then 5 mL of dichloro methane (MDC), 50 mg of dimethyl amino pyridine (DMAP) was added to RM and diisopropyl amine (0.16 mL, 1.16 mmol) was slowly added to reaction mixture at 0° C. Stir the reaction mixture for 3 hours at 50° C. The reaction mixture was poured in to ice cold water and the mixture extracted with ethyl acetate. The organic layer was washed with brine, dried over sodium sulfate, and concentrated under vacuum. The residue was purified using column chromatographyby eluting with 10% methanol in chloroform to obtain N-(3-O-acetyl-11-keto-β-boswelloyl)-diisopropylamine (28). [Yield: 200 mg; yield 34.6%]. $^1$HNMR ($CDCl_3$): δ 6.12 (1H, s), 5.54 (1H, s), 3.43 (2H, m), 2.51 (1H, m), 2.42 (2H, s), 2.27 (1H, m), 2.08 (3H, s), 1.98 (2H, m), 1.90 (2H, m), 1.77-1.56 (8H, m), 1.55-1.47 (5H, m), 1.41 (3H, s), 1.39 (12H, d, J=6.4 Hz), 1.34 (3H, s), 1.21 (3H, s), 1.12 (3H, s), 0.94 (3H, s), 0.82 (3H, s), 0.80 (3H, d, J=6.4 Hz); LCMS (m/z): 596 $(M+H)^+$.

Example 2

Preparation of n-Butylamine amide of 3-O-acetyl-11-keto-β-boswellic acid (29)

A mixture of 3-O-acetyl-11-keto-β-boswellic acid (500 mg, 0.976 mmol), 0.5 mL of $SOCl_2$ was taken in a RB. The RM was heated at 90° C. for 1 h. Then the RM was dried under high vacuum. Then 5 mL of MDC, 50 mg of DMAP, n-Butyl amine (0.117 mL, 1.17 mmol) was added to RM at RT. Then RM was stirred at RT for overnight. The RM was poured into ice cold water and extracted with EtOAc. The organic layer was washed with brine, dried over $Na_2SO_4$ and concentrated under vacuum. Crude: 500 mg. The residue was purified over silica column using 10% methanol/chloroform to obtain N-(3-O-acetyl-11-keto-β-boswelloyl)-butylamine (29). [Yield: 300 mg; yield 54.24%]. $^1$HNMR($CDCl_3$): δ 5.55 (1H, s), 5.40 (1H, t, J=5.6 Hz), 5.30 (1H, t, J=2.8 Hz), 3.22 (2H, m), 2.51 (1H, m), 2.42 (1H, s), 2.27 (1H, m), 2.08 (3H, s), 1.98 (2H, m), 1.94-1.67 (4H, m), 1.55-1.47 (5H, m), 1.35 (3H, s), 1.21 (3H, s), 1.14 (3H, s), 1.13 (3H, s), 0.94 (3H, d, J=2.4 Hz), 0.92 (3H, s), 0.82 (3H, s), 0.80 (3H, d, J=6.4 Hz); LCMS (m/z): 568 $(M+H)^+$.

Example 3

Preparation of isopropyl amine amide of 3-O-acetyl-11-keto-β-boswellic acid (30)

A mixture of 3-O-acetyl-11-keto-β-boswellic acid (500 mg, 0.976 mmol), 0.5 mL of $SOCl_2$ was taken in a RB. Then the RM was heated at 90° C. for 1 h. Then the RM was dried under high vacuum. Then 5 mL of MDC, 50 mg of DMAP, isopropyl amine (0.125 mL, 1.46 mol) was added to the RM. Then the RM was stirred at RT for 4 h. Then RM was poured into ice cold water and extracted with EtOAc. The organic layer was separated and washed with brine, dried over $Na_2SO_4$ and concentrated. Crude: 500 mg. The residue was purified over silica column using 10% methanol/chloroform to obtain N-(3-O-acetyl-11-keto-β-boswelloyl)-isopropylamine (30). [Yield: 400 mg; yield 72.3%]. $^1$HNMR ($CDCl_3$): δ 5.54 (1H, s), 5.28 (1H, s), 5.24 (1H, d, J=7.8 Hz), 4.082 (1H, m), 2.51 (1H, m), 2.42 (2H, s), 2.27 (1H, m), 2.08 (3H, s), 1.98 (2H, m), 1.90 (2H, m), 1.77-1.56 (8H, m), 1.55-1.47 (5H, m), 1.41 (3H, s), 1.39 (6H, d, J=6.4 Hz), 1.34 (3H, s), 1.21 (3H, s), 1.12 (3H, s), 0.94 (3H, s), 0.82 (3H, s), 0.80 (3H, d, J=6.4 Hz); LCMS (m/z): 553 $(M+Na^-)$.

Example 4

Preparation of dimethyl amine amide of 3-O-acetyl-11-keto-β-boswellic acid (31)

A mixture of 3-O-acetyl-11-keto-β-boswellic acid (500 mg, 0.976 mol), 0.5 mL of $SOCl_2$ was taken in a RB. Then the RM was heated at 90° C. for 1 h. Then the RM was dried under high vacuum. Then 5 mL of MDC, 50 mg of DMAP, 40% dimethyl amine (0.5 mL, 4.4 mmol) was added to the RM. Then the RM was stirred at RT for overnight. Then RM was poured into ice cold water and extracted with EtOAc. The organic layer was washed with brine, dried over $Na_2SO_4$ and concentrated under vacuum. Crude: 500 mg. The residue was purified over silica column using 25% of EtOAc in hexane to obtain N-(3-O-acetyl-11-keto-β-boswelloyl)-isopropylamine (31). [Yield: 250 mg. yield 47.5%]. $^1$HNMR ($CDCl_3$): δ 5.73 (1H, m), 5.54 (1H, s), 3.03 (6H, s), 2.51 (1H, m), 2.42 (2H, s), 2.27 (1H, m), 2.08 (3H, s), 1.98 (2H, m), 1.90 (2H, m), 1.77-1.56 (8H, m), 1.55-1.47 (5H, m), 1.41 (3H, s), 1.34 (3H, s), 1.21 (3H, s), 1.12 (3H, s), 0.94 (3H, s), 0.82 (3H, s), 0.80 (3H, d, J=6.4 Hz); LCMS (m/z): 540 $(M+H)^+$.

Example 5

Preparation of N-(3-O-acetyl-11-keto-β-boswelloyl)-glycine (32)

A mixture of 3-O-acetyl-11-keto-β-boswellic acid (500 mg, 0.976 mmol), 0.5 mL of $SOCl_2$ was taken in a RB. Then the RM was heated at 90° C. for 1 h. Then the RM was dried under high vacuum. Then 5 mL of MDC, 50 mg of DMAP, methylester of glycine (260 mg, 2.9 mmol) was added to the RM. Then the RM was stirred at RT for overnight. Then RM was poured into ice cold water and extracted with EtOAc. The organic layer was washed with brine, dried over $Na_2SO_4$ and concentrated under vacuum. Crude: 500 mg. The residue was purified over silica column using 10% methanol/chloroform to obtain N-(3-O-acetyl-11-keto-β-boswelloyl)-glycine (32). [Yield: 90 mg; yield 15.9%]. $^1$HNMR ($CDCl_3$): δ 6.07 (1H, t, J=4.4 Hz), 5.55 (1H, s), 5.30 (1H, s), 4.05 (2H, d, J=4.0 Hz), 3.76 (3H, s), 2.51 (1H, m), 2.42 (2H, s), 2.27 (1H, m), 2.08 (3H, s), 1.98 (2H, m), 1.90 (2H, m), 1.77-1.56 (8H, m), 1.55-1.47 (5H, m), 1.39 (6H, d, J=6.4 Hz), 1.34 (3H, s), 1.25 (6H, s), 1.21 (3H, s), 1.18 (3H, s), 1.10 (3H, s), 0.94 (3H, s), 0.82 (3H, s), 0.80 (3H, d, J=6.4 Hz); LCMS (m/z): 584 $(M+H)^+$.

Example 6

Preparation of 1,6-diaminohexane(hexamethylenediamine) amide of 3-O-acetyl-11-keto-β-boswellic acid (33)

A mixture of 3-O-acetyl-11-keto-β-boswellic acid (500 mg, 0.976 mmol), 0.5 mL of $SOCl_2$ was taken in a RB. Then the RM was heated at 90° C. for 1 h. Then the RM was dried under high vacuum. Then 5 mL of MDC, 50 mg of DMAP, hexamethylene diamine (340 mg, 2.93 mmol) was added to the RM. Then the RM was stirred at RT for overnight. Then RM was poured into ice cold water and extracted with EtOAc. The organic layer was washed with brine, dried over $Na_2SO_4$ and concentrated under vacuum. The residue was purified over silica column using 10% methanol/chloroform to obtain N-(3-O-acetyl-11-keto-β-boswelloyl)-1,6-diaminohexane (33). [Yield: 60 mg. yield 10%]. $^1$H NMR ($CDCl_3$): δ 6.01 (1H, t, J=4.4 Hz), 5.55 (1H, s), 5.29 (1H, s), 3.22 (2H, m), 3.00 (2H, t, J=6.8 Hz), 2.51 (1H, m), 2.42 (1H, s), 2.20 (1H, m), 2.08 (3H, s), 1.96 (2H, m), 1.90 (1H, m), 1.78 (6H, m), 1.55-1.47 (10H, m), 1.37 (2H, m), 1.34 (3H, s), 1.31 (4H, m), 1.19 (3H, s), 1.14 (3H, s), 1.10 (3H, s), 1.04 (1H, m), 0.94 (3H, s), 0.93 (2H, m), 0.82 (3H, s), 0.80 (3H, d, J=6.4 Hz); LCMS (m/z): 611 $(M+H)^+$.

Example 7

Preparation of 1,4-diaminobutane amide of 3-O-acetyl-11-keto-β-boswellic acid (34)

A mixture of 3-O-acetyl-11-keto-β-boswellic acid (500 mg, 0.976 mmol), 0.5 mL of $SOCl_2$ was taken in a RB. Then the RM was heated at 90° C. for 1 h. Then the RM was dried under high vacuum. Then 5 mL of MDC, 50 mg of DMAP, 1,4-diamino butane (0.148 mL, 1.7 mmol) was added to the RM. Then the RM was stirred at RT for overnight. The organic layer was washed with brine, dried over $Na_2SO_4$ and concentrated under vacuum. The residue was purified over silica column using 30% methanol/chloroform to obtain N-(3-O-acetyl-11-keto-β-boswelloyl)-1,4-diaminobutane (34). [Yield: 30 mg. yield 5.2%]. $^1$H NMR ($CDCl_3$): δ 6.40 (1H, s), 5.55 (1H, s), 5.29 (1H, s), 3.35 (1H, m), 3.17 (1H, m), 3.00 (2H, t, J=6.8 Hz), 2.51 (1H, m), 2.42 (1H, s), 2.2 (1H, m), 2.08 (3H, s), 1.96 (2H, m), 1.90 (1H, m), 1.78 (6H, m), 1.55-1.47 (8H, m), 1.37 (2H, m), 1.34 (3H, s), 1.31 (2H, m), 1.19 (3H, s), 1.14 (3H, s), 1.10 (3H, s), 1.04 (1H, m), 0.94 (3H, s), 0.93 (2H, m), 0.82 (3H, s), 0.80 (3H, d, J=6.4 Hz); LCMS (m/z): 583 $(M+H)^+$.

Example 8

Preparation of 1,7-diaminoheptane amide of 3-O-acetyl-11-keto-β-boswellic acid (35)

A mixture of 3-O-acetyl-11-keto-β-boswellic acid (500 mg, 0.976 mmol), 0.5 mL of $SOCl_2$ was taken in a RB. Then the RM was heated at 90° C. for 1 h. Then the RM was dried under high vacuum. Then 5 mL of MDC, 50 mg of DMAP, 1,7-diamino heptane (190 mg, 1.46 mmol)) was added to the RM. Then the RM was stirred at RT for overnight. Then RM was poured into ice cold water and extracted with EtOAc. The organic layer was washed with brine, dried over $Na_2SO_4$ and concentrated under vacuum. The residue was purified over silica column using 25% methanol/chloroform to obtain N-(3-O-acetyl-11-keto-β-boswelloyl)-1,7-diaminoheptane (35). [Yield: 110 mg; yield 18%]. $^1$H NMR ($CDCl_3$): δ 6.00 (1H, t, J=4.4 Hz), 5.55 (1H, s), 5.29 (1H, s), 3.22 (5H, m), 3.00 (2H, t, J=6.8 Hz), 2.51 (2H, m), 2.42 (1H, s), 2.29 (2H, m), 2.08 (3H, s), 1.96 (2H, m), 1.90 (1H, m), 1.78 (6H, m), 1.55-1.47 (10H, m), 1.37 (2H, m), 1.34 (3H, s), 1.31 (4H, m), 1.19 (3H, s), 1.14 (3H, s), 1.10 (3H, s), 1.04 (1H, m), 0.94 (3H, s), 0.93 (2H, m), 0.82 (3H, s), 0.80 (3H, d, J=6.4 Hz); LCMS (m/z): 625 $(M+H)^+$.

Example 9

Preparation of morpholine amide of 3-hydroxy-11-keto-β-boswellic acid (36)

A mixture of 3-hydroxy-11-keto-β-boswellic acid (500 mg, 1.06 mmol), thionyl chloride (0.5 mL), allowed to reflux for 0.5 h and evaporated. Then the acid chloride was dissolved in methylene dichloride (8 mL), 50 mg of DMAP, morpholine (0.140 mL, 1.58 mmol) was added at 0° C. and stirred at Room temperature (RT) for 2 hours. Then reaction mixture was poured in ice cold water, extracted with EtOAc. The organic layer was washed with brine, dried over sodium sulphate and concentrated. The crude was subjected to column chromatography using hexane/EtOAc mixtures as eluents to obtain N-(3-hydroxy-11-keto-β-boswelloyl)-morpholine (36). Compound eluted in 10% methanol in chloroform. [Yield 200 mg. Percentage of yield is 32.7%]. $^1$HNMR ($CDCl_3$): δ 5.57 (1H, brs), 3.69 (4H, m), 3.58 (5H, m), 2.51 (1H, m), 2.42 (1H, s), 2.30 (1H, m), 2.26 (1H, m), 2.05 (2H, m), 1.94 (1H, m), 1.67 (4H, m), 1.55-1.47 (2H, m), 1.37 (5H, m), 1.32 (3H, s), 1.21 (3H, s), 1.14 (3H, s), 1.13 (3H, s), 0.94 (3H, d, J=2.4 Hz), 0.92 (3H, s), 0.82 (3H, s), 0.80 (3H, d, J=6.4 Hz); LCMS (m/z): 540 $(M+H)^+$.

Example 10

Preparation of morpholine amide of 3-O-acetyl-11-keto-β-boswellic acid (37)

A mixture of 3-O-acetyl-11-keto-β-boswellic acid (500 mg, 0.976 mmol), thionyl chloride (0.5 mL), allowed to reflux for 0.5 h and evaporated. Then the acid chloride was dissolved in methylene dichloride (8 mL), 50 mg of DMAP, morpholine (0.128 mL, 1.5 mmol) was added at 0° C. and stirred at Room temperature (RT) for 2 hours. Then reaction mixture was poured in ice cold water and extracted with EtOAc. The organic layer was washed with brine, dried over sodium sulphate and concentrated. The crude was subjected to column chromatography, hexane/EtOAc as an eluent. The fraction eluted with 20% ethylacetate in hexane yielded N-(3-O-acetyl-11-keto-β-boswelloyl)-morpholine (37). [Yield 200 mg. Percentage of yield is 35%]. $^1$HNMR ($CDCl_3$): δ 5.57 (1H, brs), 5.55 (1H, brs), 3.69 (4H, m), 3.58 (4H, m), 2.51 (1H, m), 2.42 (1H, s), 2.30 (1H, m), 2.27 (1H, m), 2.12 (3H, s), 2.05 (2H, m), 1.94 (1H, m), 1.67 (4H, m), 1.55-1.47 (5H, m), 1.37 (2H, m), 1.32 (3H, s), 1.21 (3H, s), 1.14 (3H, s), 1.13

(3H, s), 0.94 (3H, d, J=2.4 Hz), 0.92 (3H, s), 0.82 (3H, s), 0.80 (3H, d, J=6.4 Hz); LCMS (m/z): 604 (M+Na)$^+$.

Example 11

Preparation of 2-piperazinoethanol amide of 3-hydroxy-11-keto-β-boswellic acid (38)

A mixture of 3-hydroxy-11-keto-β-boswellic acid (500 mg, 1.06 mmol), thionylchloride (0.5 mL), allowed to reflux for 0.5 h and evaporated. Then the acid chloride was dissolved in methylene dichloride (8 mL), 50 mg of DMAP, 2-piperazinoethanol (0.195 mL, 1.59 mmol) was added at 0° C. and stirred at Room temperature (RT) for 2 hours. Then reaction mixture was poured in ice cold water and extracted with EtOAc. The organic layer was washed with brine, dried over sodium sulphate and concentrated under vacuum. N-(3-hydroxy-11-keto-β-boswelloyl)-2-piperazinoethanol (38) was eluted with 30% ethyl acetate in hexane. [Yield 220 mg. Percentage of yield is 33.9%]. $^1$H NMR (CDCl$_3$): δ 5.57 (1H, brs), 3.92-3.65 (10H, m), 2.92-2.78 (3H, m), 2.51 (1H, m), 2.42 (1H, s), 2.30 (1H, m), 2.26 (1H, m), 2.05 (2H, m), 1.94 (1H, m), 1.67 (4H, m), 1.55-1.47 (2H, m), 1.37 (5H, m), 1.32 (3H, s), 1.21 (3H, s), 1.14 (3H, s), 1.13 (3H, s), 0.94 (3H, d, J=2.4 Hz), 0.92 (3H, s), 0.82 (3H, s), 0.80 (3H, d, J=6.4 Hz); LCMS (m/z): 583 (M+H)$^+$.

Example 12

Preparation of 2-piperazinoethanol amide of 3-O-acetyl-11-keto-β-boswellic acid (39)

A mixture of 3-O-acetyl-11-keto-β-boswellic acid (500 mg, 0.976 mmol), thionyl chloride (0.5 mL), allowed to reflux for 0.5 h and evaporated. Then the acid chloride was dissolved in methylene dichloride (8 mL), 50 mg of DMAP, Piperazine-1-ethanol (0.179 mL, 1.45 mmol) was added at 0° C. and stirred at Room temperature (RT) for 2 hours. Then reaction mixture was poured into ice cold water and extracted with EtOAc. The organic layer was washed with brine, dried over sodium sulphate and concentrated. The crude was subjected to column chromatography using hexane/EtOAc mixtures as eluents. The fraction eluted with 30% hexane/ethyl acetate yielded N-(3-O-acetyl-11-keto-β-boswelloyl)-2-piperazinoethanol (39). [Yield 230 mg. Percentage of yield is 38%]. $^1$HNMR (CDCl$_3$): δ 5.57 (1H, brs), 5.55 (1H, brs), 3.92-3.65 (9H, m), 2.92-2.78 (3H, m), 2.51 (1H, m), 2.42 (1H, s), 2.30 (1H, m), 2.26 (1H, m), 2.12 (3H, s), 2.05 (2H, m), 1.94 (1H, m), 1.67 (4H, m), 1.55-1.47 (2H, m), 1.37 (5H, m), 1.32 (3H, s), 1.21 (3H, s), 1.14 (3H, s), 1.13 (3H, s), 0.94 (3H, d, J=2.4 Hz), 0.92 (3H, s), 0.82 (3H, s), 0.80 (3H, d, J=6.4 Hz); LCMS (m/z): 625 (M+H)$^+$.

Example 13

Preparation of Imidazole amide of 3-O-acetyl-11-keto-β-boswellic acid (40)

A mixture of 3-O-acetyl-11-keto-β-boswellic acid (500 mg, 0.976 mmol), thionyl chloride (0.5 mL), allowed to reflux for 0.5 h and evaporated. Then the acid chloride was dissolved in methylene dichloride (8 mL), 50 mg of DMAP, Imidazole (0.099 g, 1.46 mmol) was added at 0° C. and stirred at Room temperature (RT) for 2 hours. Then reaction mixture was poured in ice cold water and extracted with EtOAc. The organic layer was washed with brine, dried over sodium sulphate and concentrated. The crude was subjected to column chromatography using hexane/EtOAc mixtures. N-(3-O-acetyl-11-keto-β-boswelloyl)-imadazole (40) was eluted into 30% hexane/ethyl acetate fraction. [Yield 300 mg. Percentage of yield is 54.7%]. $^1$H NMR (CDCl$_3$): δ 8.32 (1H, s), 7.66 (1H, s), 7.07 (1H, s), 5.57 (1H, brs), 5.55 (1H, brs), 2.51 (1H, m), 2.42 (1H, s), 2.30 (1H, m), 2.27 (1H, m), 2.12 (3H, s), 2.05 (2H, m), 1.94 (1H, m), 1.67 (4H, m), 1.55-1.47 (2H, m), 1.37 (5H, m), 1.32 (3H, s), 1.21 (3H, s), 1.14 (3H, s), 1.13 (3H, s), 0.94 (3H, d, J=2.4 Hz), 0.92 (3H, s), 0.82 (3H, s), 0.80 (3H, d, J=6.4 Hz); LCMS (m/z): 585 (M+Na)$^+$.

Example 14

Preparation of 2-aminoindan amide of 3-O-acetyl-11-keto-β-boswellic acid (41)

A mixture of 3-O-acetyl-11-keto-β-boswellic acid (500 mg, 0.976 mmol), thionyl chloride (0.5 mL), allowed to reflux for 0.5 h and evaporated. Then the acid chloride was dissolved in methylene dichloride (8 mL), 50 mg of DMAP, 2-aminoindan (196 mg, 1.47 mmol) was added at 0° C. and stirred at Room temperature (RT) for 2 hours. The reaction mixture was poured in ice cold water and extracted with EtOAc. The organic layer was washed with brine, dried over sodium sulphate and concentrated. The residue was subjected to column chromatography using hexane/EtOAc mixtures. The fraction eluted with 40% hexane/ethyl acetate yielded N-(3-O-acetyl-11-keto-β-boswelloyl)-2-aminoindan (41). Yield 340 mg. [Percentage of yield is 55.5%]. $^1$HNMR (CDCl$_3$): δ 7.23-7.13 (4H, m), 5.53 (1H, s), 5.46 (1H, t, J=5.2 Hz), 5.29 (1H, brs), 3.59-3.42 (2H, m), 2.91-2.80 (2H, m), 2.51 (1H, m), 2.42 (1H, s), 2.30 (1H, m), 2.27 (1H, m), 2.12 (3H, s), 2.05 (2H, m), 1.94 (1H, m), 1.67 (4H, m), 1.55-1.47 (2H, m), 1.37 (5H, m), 1.32 (3H, s), 1.21 (3H, s), 1.14 (3H, s), 1.13 (3H, s), 0.94 (3H, d, J=2.4 Hz), 0.92 (3H, s), 0.82 (3H, s), 0.80 (3H, d, J=6.4 Hz); LCMS (m/z): 628 (M+H)$^+$.

Example 15

Preparation of aniline amide of 3-O-acetyl-11-keto-β-boswellic acid (42)

A mixture of 3-O-acetyl-11-keto-β-boswellic acid (500 mg, 0.976 mmol), thionyl chloride (0.5 mL), allowed to reflux for 0.5 h and evaporated. Then the acid chloride was dissolved in methylene dichloride (8 mL), 50 mg of DMAP, aniline (0.26 mL, 2.3 mmol) was added and allowed to RT for 2 hours. The reaction mixture was poured in ice cold water and extracted with EtOAc. The organic layer was washed with brine, dried over sodiumsulphate and concentrated. The crude mixture was subjected to column chromatography using hexane/EtOAc mixtures. The fraction eluted with 15-20% hexane/ethyl acetate yielded N-(3-O-acetyl-11-keto-β-boswelloyl)-aniline (42) [Yield—220 mg. % of yield—37.5]. $^1$H NMR (CDCl$_3$): δ 7.44 (2H, d, J=8.4 Hz), 7.33 (2H, t, J=7.8 Hz), 7.15 (1H, s), 7.12 (1H, t, J=7.8 Hz), 5.56 (1H, s), 5.34 (1H, brs), 2.60 (1H, m), 2.45 (1H, s), 2.38 (1H, m), 2.10 (3H, s), 2.02 (1H, m), 1.92 (2H, m), 1.90 (2H, m), 1.82 (1H, m), 1.78 (2H, m), 1.69 (1H, m), 1.60 (1H, m), 1.55-1.47 (2H, m), 1.4 (1H, s), 1.37 (2H, m), 1.34 (3H, s), 1.19 (3H, s), 1.14 (3H, s), 1.10 (3H, s), 1.04 (1H, m), 0.94 (3H, s), 0.93 (2H, m), 0.82 (3H, s), 0.8 (3H, d, J=6.4 Hz); LCMS (m/z): 588 (M+H)$^+$.

Example 16

Preparation of methyl amine amide of 3-O-acetyl-11-keto-β-boswellic acid (43)

A mixture of 3-O-acetyl-11-keto-β-boswellic acid (500 mg, 0.976 mmol), thionylchloride (0.5 mL), allowed to reflux for 0.5 h and evaporated. Then the acid chloride was dissolved in methylene dichloride (8 mL), 50 mg of DMAP, methyl amine hydrochloride (500 mg, 7.4 mmol) was added and allowed to RT for 2 hours. The reaction mixture was poured into ice cold water and extracted with EtOAc. The organic layer was washed with brine, dried over sodium sulphate and concentrated. The crude mixture was subjected to column chromatography using hexane/EtOAc mixtures. The fraction eluted with 15-20% hexane/ethyl acetate yielded N-(3-O-acetyl-11-keto-β-boswelloyl)-methylamine (43). [Yield—230 mg. % of yield 41.5]. $^1$HNMR (CDCl$_3$): δ 5.55 (1H, brs), 5.49 (1H, m), 5.32 (1H, brs), 2.79 (3H, d, J=4.4 Hz), 2.51 (1H, m), 2.42 (1H, s), 2.20 (1H, m), 2.08 (3H, s), 1.96 (2H, m), 1.90 (1H, m), 1.78 (2H, m), 1.55-1.47 (4H, m), 1.40 (2H, m), 1.37 (2H, m), 1.34 (3H, s), 1.31 (2H, m), 1.19 (3H, s), 1.14 (3H, s), 1.10 (3H, s), 1.04 (1H, m), 0.94 (3H, s), 0.93 (2H, m), 0.82 (3H, s), 0.8 (3H, d, J=6.4 Hz); LCMS (m/z): 526 (M+H)$^+$.

Example 17

Preparation of 2-Bromoaniline amide of 3-O-acetyl-11-keto-β-boswellic acid (44)

A mixture of 3-O-acetyl-11-keto-β-boswellic acid (500 mg, 0.976 mmol), thionylchloride (0.5 mL), allowed to reflux for 0.5 h and evaporated. Then the acid chloride was dissolved in methylene dichloride (8 mL), 50 mg of DMAP, 2-bromoaniline (0.33 mL, 2.3 mmol) and allowed to Room temperature and stirred for 2 hours. The reaction mixture was poured in ice cold water and extracted with EtOAc. The organic layer was wash with brine, dried over sodium sulphate and concentrated. The residue was subjected to column chromatography using hexane/EtOAc mixtures. N-(3-O-acetyl-11-keto-β-boswelloyl)-bromoaniline (44) was eluted into 15-20% hexane/ethyl acetate. [Yield—310 mg. % of yield—47.7]. $^1$HNMR (CDCl$_3$): δ 8.26 (1H, dd, J=1.6, 8.4 Hz), 7.71 (1H, s), 7.53 (1H, dd, J=1.2, 8.0 Hz), 7.31 (1H, t, J=7.2 Hz), 6.97 (1H, t, J=6.4 Hz), 5.55 (1H, s), 5.45 (1H, brs), 3.7 (1H, m), 2.51 (2H, m), 2.42 (1H, s), 2.08 (2H, m), 2.02 (1H, m), 1.92 (2H, m), 1.90 (2H, m), 1.82 (1H, m), 1.78 (2H, m), 1.69 (1H, m), 1.60 (1H, m), 1.55-1.47 (2H, m), 1.40 (1H, s), 1.37 (2H, m), 1.34 (3H, s), 1.19 (3H, s), 1.14 (3H, s), 1.10 (3H, s), 1.04 (1H, m), 0.94 (3H, s), 0.93 (2H, m), 0.82 (3H, s), 0.80 (3H, d, J=6.4 Hz); LCMS (m/z): 666 (M+H)$^+$.

Example 18

Preparation of N-(Methyl)ethanol amine amide of 3-O-acetyl-11-keto-β-boswellic acid (45)

A mixture of 3-O-acetyl-11-keto-β-boswellic acid (500 mg, 0.976 mmol), thionylchloride (0.5 mL), allowed to reflux for 0.5 h and evaporated. Then the acid chloride was dissolved in methylene dichloride (8 mL), 50 mg of DMAP, N-(Methyl) ethanol amine (0.23 mL, 2.3 mmol) was added and allowed to RT for 2 hours. The reaction mixture was poured into ice cold water and extracted with EtOAc. The organic layer was washed with brine, dried over sodium sulphate and concentrated. The crude mixture was subjected to column chromatography using hexane/EtOAc mixtures. The fraction eluted with 15-20% hexane/ethyl acetate N-(3-O-acetyl-11-keto-β-boswelloyl)-N-(methyl)ethanol (45). [Yield—110 mg. % of yield—20.3]. $^1$HNMR (CDCl$_3$): δ 5.77 (1H, brs), 5.55 (1H, s), 3.79 (2H, m), 3.70 (1H, m), 3.32 (1H, m), 3.20 (3H, s), 2.51 (1H, m), 2.42 (1H, s), 2.20 (1H, m), 2.08 (3H, s), 1.96 (2H, m), 1.90 (1H, m), 1.78 (2H, m), 1.55-1.47 (4H, m), 1.37 (2H, m), 1.34 (3H, s), 1.31 (2H, m), 1.19 (3H, s), 1.14 (3H, s), 1.10 (3H, s), 1.04 (1H, m), 0.94 (3H, s), 0.93 (2H, m), 0.82 (3H, s), 0.80 (3H, d, J=6.4 Hz); LCMS (m/z): 570 (M+H)$^-$.

Example 19

Preparation of 4-hydroxyaniline amide of 3-O-acetyl-11-keto-β-boswellic acid (46)

A mixture of 3-O-acetyl-11-keto-β-boswellic acid (500 mg, 0.976 mmol), thionylchloride (0.5 mL), allowed to reflux for 0.5 h and evaporated. Then the acid chloride was dissolved in methylene dichloride (8 mL), 50 mg of DMAP, 4-hydroxyaniline (0.319 mL, 2.3 mmol) was added and allowed to RT for 2 hours. The reaction mixture was poured into ice cold water and extracted with EtOAc. The organic layer was washed with brine, dried over sodium sulphate and concentrated under vacuum. The crude mixture was subjected to column chromatography using hexane/EtOAc mixtures. The fraction eluted with 15-20% hexane/ethyl acetate yielded N-(3-O-acetyl-11-keto-β-boswelloyl)-4-hydroxyaniline (46). [Yield—80 mg. % of yield—13.6]. $^1$H NMR (CDCl$_3$): δ 6.84 (2H, d, J=8.8 Hz), 6.66 (2H, d, J=8.4 Hz), 5.55 (1H, s), 5.4 (1H, brs), 3.70 (1H, m), 2.51 (2H, m), 2.42 (1H, s), 2.29 (2H, m), 2.08 (3H, s), 1.96 (2H, m), 1.90 (2H, m), 1.78 (2H, m), 1.55-1.47 (4H, m), 1.37 (2H, m), 1.34 (3H, s), 1.23 (1H, m), 1.19 (3H, s), 1.14 (3H, s), 1.10 (3H, s), 1.04 (1H, m), 0.94 (3H, s), 0.93 (2H, m), 0.82 (3H, s), 0.80 (3H, d, J=6.4 Hz); LCMS (m/z): 604 (M+H)$^+$.

Example 20

Preparation of N-(3-O-acetyl-11-keto-β-boswelloyl)-phenyl hydrazine (47)

A mixture of 3-O-acetyl-11-keto-β-boswellic acid (500 mg, 0.976 mmol), thionylchloride (0.5 mL), allowed to reflux for 0.5 h and evaporated. Then the acid chloride was dissolved in methylenedichloride (8 mL), 50 mg of DMAP, phenyl hydrazine hydrochloride (500 mg, 4.6 mmol) was added at 0° C. and allowed to reflux for 2 hours. The reaction mixture was poured in ice cold water and the mixture extracted with EtOAc. The organic layer was wash with brine, dried over sodium sulphate and concentrated. The residue was subjected to column chromatography using hexane/EtOAc mixtures. The N-(3-O-acetyl-11-keto-β-boswelloyl)-phenyl hydrazine (47) was eluted with 15-20% hexane/ethyl acetate mixture. [Yield—260 mg. % of yield 45]. $^1$HNMR (CDCl$_3$): δ 7.59 (1H, s), 7.21 (3H, t, J=7.8 Hz), 6.89 (1H, t, J=7.2 Hz), 6.83 (2H, d, J=8.0 Hz), 6.17 (1H, brs), 5.55 (1H, s), 5.37 (1H, s), 2.51 (2H, m), 2.42 (1H, s), 2.29 (2H, m), 2.08 (3H, s), 1.96 (2H, m), 1.90 (1H, m), 1.78 (2H, m), 1.55-1.47 (4H, m), 1.37 (2H, m), 1.34 (3H, s), 1.23 (1H, m), 1.19 (3H, s), 1.14 (3H, s), 1.10 (3H, s), 1.04 (1H, m), 0.94 (3H, s), 0.93 (2H, m), 0.82 (3H, s), 0.80 (3H, d, J=6.4 Hz); LCMS (m/z): 601 (M−H)$^+$.

Example 21

Formylation of N-(3-O-acetyl-11-keto-β-boswelloyl)-ethylene diamine to obtain N-(3-O-acetyl-11-keto-β-boswelloyl)-[2'-N-formyl]ethylenediamine (48)

A mixture of ethylene diamine amide of 3-O-acetyl-11-keto-β-boswellic acid (21, 200 mg, 0.3610 mmol), 2 ml of DMF, 52 ml of tri ethyl amine, 13.8 ml of formic acid was taken in a R.B. flask. Reaction mixture was heated at 100° C. for 2 h. The R.M. was cooled and poured in to ice cold water and extracted with EtOAc. The organic layer was washed with water and brine, dried over $Na_2SO_4$ and concentrated. Crude weight: 220 mg. The residue was subjected to column chromatography over silica gel using methanol/chloroform mixtures. The fraction eluted with 5% MeOH in $CHCl_3$ yielded N-(3-O-acetyl-11-keto-β-boswelloyl)-[2'-N-formyl] ethylenediamine (48) [Yield was 110 mg; yield 52.38%]. ¹HNMR ($CDCl_3$): δ 8.18 (1H, s), 6.47 (1H, brs), 6.25 (1H, brs), 5.55 (1H, s), 5.30 (1H, s), 4.12 (1H, m), 3.47 (4H, m), 2.53 (1H, m), 2.42 (1H, s), 2.30 (1H, m), 2.08 (3H, s), 1.96 (2H, m), 1.90 (1H, m), 1.78 (2H, m), 1.55-1.47 (5H, m), 1.37 (2H, m), 1.34 (3H, s), 1.31 (2H, m), 1.19 (3H, s), 1.14 (3H, s), 1.10 (3H, s), 1.04 (1H, m), 0.94 (3H, s), 0.93 (2H, m), 0.82 (3H, s), 0.80 (3H, d, J=6.4 Hz); LCMS (m/z): 605 (M+Na)⁺.

Example 22

Preparation of N-(3-O-acetyl-11-keto-β-boswelloyl)-[2'-N,N-diethylchloro)ethylene diamine (49)

A mixture of ethylene diamine amide of 3-O-acetyl-11-keto-β-boswellic acid (1.0 g, 0.0018 mol) prepared above, 18 ml of acetone, $K_2CO_3$ (1.49 g, 0.0108 mol), KI (0.059 g, 0.0003 mol) was taken in a R.B. flask. Finally added chloroethanol (0.6 ml, 0.009 mol) and stir well for 5 days at R.T. Then R.M. was filtered, washed with acetone and the filtrate was concentrated. The crude mixture was subjected to silica column chromatography using methanol/$CHCl_3$ mixtures. Fraction eluted with 15% methanol/$CHCl_3$ yielded N-(3-O-acetyl-11-keto-β-boswelloyl)-[2'-N,N-diethylchloro)ethylene diamine (49). [Yield: 1.0 g (LI/SCR-57). % of yield: 86]. ¹HNMR ($CDCl_3$): δ 6.50 (1H, t, J=4.8 Hz), 5.55 (1H, s), 5.33 (1H, s), 3.72 (2H, t, J=4.8 Hz), 3.41 (2H, t, J=5.6 Hz), 3.36 (4H, m), 2.86 (4H, m), 2.53 (1H, d, J=12.8 Hz), 2.41 (1H, s), 2.30 (1H, m), 2.08 (3H, s), 1.96 (1H, s), 1.85 (1H, m), 1.70 (1H, m), 1.62 (1H, m), 1.51 (4H, m), 1.40 (2H, m), 1.37 (3H, s), 1.34 (3H, s), 1.26 (3H, m), 1.19 (3H, s), 1.16 (3H, s), 1.12 (3H, s), 1.05 (1H, m), 0.95 (3H, s), 0.82 (3H, s), 0.80 (3H, d, J=6.4 Hz); LCMS (m/z): 643 (M+H)⁺.

Example 23

Preparation of N-(3-O-acetyl-11-keto-β-boswelloyl)-[2'-(N-3,4 methylene dioxy cinnamoyl)]-ethylene diamine (50)

A mixture of 3,4-(methylenedioxy) cinnamic acid (280 mg, 1.35 mmol) and $SOCl_2$ (0.5 mL) was refluxed under stirring. After 0.5 h, excess $SOCl_2$ was evaporated. The residue was dissolved in methylene chloride (8 mL) and the mixture treated with ethylene diamine amide of 3-O-acetyl-11-keto-β-boswellic acid (500 mg, 0.902 mmol) at 0° C. and the mixture kept under stirring for 2 h. The reaction mixture was poured into ice cold water and extracted with EtOAc. The organic layer was washed with brine, dried over sodium sulphate and concentrated. The crude mixture was subjected to column chromatography using hexane/EtOAc mixtures. The fraction eluted in 30% hexane/ethyl acetate yielded N-(3-O-acetyl-11-keto-β-boswelloyl)-[2'-(N-3,4 methylene dioxycinnamoyl)]-ethylene diamine (50). [Yield 310 mg. Percentage of yield is 50.5%]. ¹H-NMR ($CDCl_3$): δ 7.59 (1H, d, J=15.6 Hz), 7.08 (1H, brs), 6.99-6.97 (2H, m), 6.80 (1H, d, J=8 Hz), 6.56 (1H, d, 15.2 Hz), 6.00 (2H, s), 4.09 (1H, m), 3.75 (1H, m), 3.59-3.42 (2H, m), 2.91-2.80 (2H, m), 2.51 (1H, m), 2.42 (1H, s), 2.30 (1H, m), 2.267 (1H, m), 2.12 (3H, s), 2.05 (2H, m), 1.94 (1H, m), 1.67 (4H, m), 1.55-1.47 (2H, m), 1.37 (5H, m), 1.32 (3H, s) 1.21 (3H, s), 1.14 (3H, s), 1.13 (3H, s), 0.94 (3H, d, J=2.4 Hz), 0.92 (3H, s), 0.82 (3H, s), 0.80 (3H, d, J=6.4 Hz). LCMS (m/z): 628 (M+H)⁺.

Example 24

Preparation of N-(3-O-acetyl-β-boswelloyl)-ethylenediamine (51)

A mixture of 3-O-acetyl-beta-boswellic acid (500 mg, 1 mmol) and 0.5 mL of $SOCl_2$ in a R.B. flask was refluxed for 1 hour and the mixture was evaporated under high vacuum. Then, 30 ml of THF and 30 mL of MDC were added to the residue treated with ethylene di amine (0.66 mL, 10 mmol) and DMAP (10 mg) at 10° C. Then RM was stirred at RT for 3 hours. The reaction mixture was poured in to ice cold water and extracted with EtOAc. The organic layer was washed with brine, dried over $Na_2SO_4$ and concentrated. The residue subjected to column chromatography over silica using acetone/$CHCl_3$ mixtures to obtain N-(3-O-acetyl-(β)-boswelloyl)-ethylenediamine (51) in the fraction eluted with 40% acetone/$CHCl_3$. [270 mg. Yield: 50%]. ¹H-NMR ($CDCl_3$): δ 6.20 (1H, brs), 5.36 (1H, brs), 5.15 (1H, brs), 3.35 (2H, m), 2.80 (2H, brs), 2.51 (1H, m), 2.42 (1H, s), 2.2 (1H, m), 2.08 (3H, s), 1.96 (2H, m), 1.90 (1H, m), 1.78 (6H, m), 1.55-1.47 (6H, m), 1.37 (2H, m), 1.31 (2H, m), 1.28 (4H, m), 1.12 (3H, s), 1.05 (3H, s), 0.91 (3H, s), 0.88 (3H, s), 0.87 (3H, s), 0.80 (6H, s). LCMS (m/z): 541 (M+H)⁺.

Example 25

Preparation of ammonia amide of 3-O-acetyl-beta-boswellic acid (52)

A mixture of 3-O-acetyl-β-boswellic acid (500 mg, 1.0 mmol) and thionyl chloride (0.5 mL), was allowed to reflux for 0.5 h and then evaporated. The acid chloride so obtained was dissolved in methylene dichloride (8 mL) treated with ammonium hydroxide (28% aqueous solution) (0.5 ml) at 0° C. and the mixture stirred at Room temperature (RT) for 2 hours. The reaction mixture was poured in ice cold water and extracted with EtOAc. The organic layer was washed with brine, dried over sodium sulphate and concentrated. The crude was subjected to column chromatography using hexane/EtOAc mixture. The fraction eluted with 30% hexane/ethyl acetate yielded N-(3-O-acetyl-β-boswelloyl)-ammonia (52). [Yield 400 mg; Percentage of yield 81%]. ¹H-NMR ($CDCl_3$): δ 5.35 (1H, brs), 5.16 (1H, t, J=5.6 Hz), 2.2 (1H, m), 2.08 (3H, s), 1.96 (2H, m), 1.90 (1H, m), 1.78 (6H, m), 1.55-1.47 (6H, m), 1.37 (2H, m), 1.31 (2H, m), 1.28 (4H, m), 1.16 (1H, m), 1.12 (3H, s), 1.05 (3H, s), 0.91 (3H, s), 0.88 (3H, s), 0.87 (3H, s), 0.80 (6H, s). LCMS (m/z): 498 (M+H)⁺.

Example 26

Preparation of ethanolamine amide of 3-O-acetyl-beta-boswellic acid (53)

A mixture of 3-O-acetyl-β-boswellic acid (500 mg, 1.0 mmol) and thionyl chloride (0.5 mL) was allowed to reflux for 0.5 h and the mixture was evaporated. The acid chloride was dissolved in methylene dichloride (8 mL) and treated with ethanolamine (0.088 mL, 1.5 mmol) at 0° C. and stirring continued at room temperature (RT) for 2 hours. The reaction mixture was poured in ice cold water and extracted with EtOAc. The organic layer was washed with brine, dried over sodium sulphate and concentrated. The crude was subjected to column chromatography using hexane/EtOAc mixtures.

The fraction eluted with 30% hexane/ethyl acetate yielded N-(3-O-acetyl-β-boswelloyl)-ethanolamine (53). [Yield 410 mg. Percentage of yield is 73.8%]. $^1$H-NMR (CDCl3): δ 5.37 (1H, brs), 5.16 (1H, t, J=3.6 Hz), 3.73 (2H, t, J=4.8 Hz), 3.43 (2H, m), 2.2 (1H, m), 2.08 (3H, s), 1.96 (2H, m), 1.90 (1H, m), 1.78 (5H, m), 1.55-1.47 (6H, m), 1.37 (2H, m), 1.31 (2H, m), 1.28 (4H, m), 1.16 (1H, m), 1.12 (3H, s), 1.05 (3H, s), 0.91 (3H, s), 0.88 (3H, s), 0.87 (3H, s), 0.80 (6H, s). LCMS (m/z): 542 $(M+H)^+$.

Example 27

Preparation of Piperazine amide of 3-O-acetyl-beta-boswellic acid (54)

A mixture of 3-O-acetyl-β-boswellic acid (500 mg, 1.0 mmol), thionylchloride (0.5 mL), allowed to reflux for 0.5 h and evaporated. Then the acid chloride was dissolved in methylene dichloride (8 mL) and treated with piperazine (129 mg, 1.5 mmol) at 0° C. The mixture was stirred at Room temperature (RT) for 2 hours. The reaction mixture was then poured into ice cold water and extracted with EtOAc. The organic layer was washed with brine, dried over sodium sulphate and concentrated. The crude was subjected to column chromatography using hexane/EtOAc mixture. The fraction eluted with 30% hexane/ethyl acetate to obtain N-(3-O-acetyl-β-boswelloyl)-piperazine (54). [Yield 380 mg. Percentage of yield is 67.1]. $^1$H-NMR (CDCl$_3$): δ 5.54 (1H, brs), 5.16 (1H, t, J=2.8 Hz), 3.69 (4H, m), 3.61 (4H, m), 2.08 (3H, s), 1.96 (2H, m), 1.90 (1H, m), 1.78 (6H, m), 1.55-1.47 (6H, m), 1.37 (2H, m), 1.31 (2H, m), 1.28 (4H, m), 1.16 (1H, m), 1.12 (3H, s), 1.05 (3H, s), 0.91 (3H, s), 0.88 (3H, s), 0.87 (3H, s), 0.80 (6H, s). LCMS (m/z): 567 $(M+H)^+$.

Example 28

Preparation of N-(3-O-acetyl-11-keto-β-boswelloyl)-[2'-N,N-dimethyl]ethylenediamine (55)

A mixture of ethylene diamine amide of 3-O-acetyl-11-keto-boswellic acid (200 mg, 0.36 mmol), 4 mL of ethanol, 10 mg of paraformaldehyde was taken in a RB flask. Then the RM was refluxed for 1 h. The RM was allowed to RT and treated with NaBH$_4$ (13.5 mg, 0.36 mmol), and the stirring continued at RT for 1 h, Then the RM was maintained reflux for 1 h. The RM was concentrated under vacuum. The residue was dissolved in CHCl$_3$, the mixture washed with NaHCO$_3$ solution followed by brine. The solution was dried over sodium sulfate and concentrated. The residue was subjected to column chromatography over silica gel and the fraction eluted 40% acetone/CHCl$_3$ yielded N-(3-O-acetyl-11-keto-β-boswelloyl)-[2'-N,N-dimethyl]ethylenediamine (55). [Yield was 40 mg; Percentage of yield: 19.5%]. $^1$H-NMR (CDCl$_3$): δ 6.24 (1H, brs), 5.55 (1H, s), 5.35 (1H, s), 4.21 (1H, t, J=6.0 Hz), 3.31 (2H, m), 2.53 (2H, m), 2.42 (1H, s), 2.3 (2H, m), 2.08 (3H, s), 1.96 (2H, m), 1.90 (1H, m), 1.85-1.65 (6H, m), 1.55-1.47 (5H, m), 1.37 (2H, m), 1.34 (3H, s), 1.31 (2H, m), 1.19 (3H, s), 1.14 (3H, s), 1.10 (3H, s), 1.04 (1H, m), 0.94 (3H, s), 0.93 (2H, m), 0.82 (3H, s), 0.8 (3H, d, J=6.4 Hz). LCMS (m/z): 569 $(M+Na)^+$.

Example 29

Preparation of Dimethyl Glutamate amide of 3-O-acetyl-11-keto-β-boswellic acid (56)

A mixture of 3-O-acetyl-11-keto-β-boswellic acid (200 mg, 0.39 mmol), 0.3 mL of SOCl$_2$ was taken in a R.B. flask. R.M. was reflux for 1 hour and then R.M. was dried under high vacuum. Methyl Glutamate (200 mg, 1.36 mmol) was dissolved in 2 mL of dry methanol. Then acid chloride of B$_2$ was dissolved in 3 mL of MDC. Glutamine solution was added to RM and stirred at R.T. for 1 hour. The RM was then stirred at 60° C. for half an hour. The reaction mixture was then poured into ice cold water and extracted with EtOAc. The organic layer was washed with brine, dried over sodium sulphate and concentrated. The crude was subjected to column chromatography using hexane/EtOAc mixtures to obtain N-(3-O-acetyl-11-keto-β-boswelloyl)-dimethyl glutamate (56). [Yield was 91 mg; percentage of yield was 34.2]. $^1$H-NMR (CDCl$_3$): δ 6.31 (1H, d, J=7.6 Hz), 5.55 (1H, s), 5.34 (1H, s), 4.65 (1H, m), 3.73 (3H, s), 3.67 (3H, s), 2.53 (1H, m), 2.41 (1H, s), 2.32 (2H, m), 2.30 (2H, m), 2.22 (1H, m), 2.08 (3H, s), 1.96 (3H, m), 1.78 (2H, m), 1.55-1.47 (4H, m), 1.43 (4H, m), 1.35 (3H, s), 1.31 (2H, m), 1.22 (3H, s), 1.16 (3H, s), 1.07 (3H, s), 1.04 (1H, m), 0.95 (3H, s), 0.88 (2H, m), 0.82 (3H, s), 0.81 (3H, d, J=6.4 Hz). LCMS (m/z): 670 $(M+H)^+$.

Example 30

Preparation of N-(3-oxime-11-keto-β-boswelloyl)-ammonia (57)

Step 1: Preparation of Ammonia amide of 3-hydroxy-11-keto-beta-boswellic acid

A mixture of 3-hydroxy-11-keto-β-boswellic acid (500 mg, 1.06 mmol), thionyl chloride (0.5 mL), allowed to reflux for 0.5 h and evaporated. Then the acid chloride was dissolved in methylene dichloride (8 mL) and treated with ammonium hydroxide (28% aqueous solution) (0.5 mL) at 0° C. and stirred at Room temperature (RT) for 2 hours. The reaction mixture was poured in ice cold water, extracted with EtOAc. The organic layer was washed with brine, dried over sodium sulphate and concentrated. The crude was subjected to column chromatography on silica using hexane/EtOAc mixtures. The fraction eluted with 35% hexane/ethyl acetate yielded amide. [Yield 330 mg; Percentage of yield 66.5].

Step 2: Oxidation of Ammonia amide of 3-hydroxy-11-keto-beta-boswellic acid

A solution of ammonia amide of 3-hydroxy-11-keto-beta-boswellic acid [2 g, 0.004264 mol] in 30 mL of MDC was taken in a RB and treated slowly with Jone's reagent (6 mL of Jone's reagent adsorbed with 12 g of silica gel) at RM and the stirring continued at RT for 1 hr. Then RM was filtered, extracted with dichloromethane. The extract was concentrated and the residue subjected to column chromatography using hexane/ethyl acetate mixtures. The 3,11-di keto ammonia amide was eluted into 25% of hexane/ethyl acetate. [Yield 1.2 g, percentage of yield was 60%].

Step 3: Obtaining 3-Oxime of Ammonia amide of 11-keto-beta-boswellic acid

A mixture of 3,11-di keto ammonia amide of beta-boswellic acid [0.8 g, 0.0017 mol] obtained above, 10 mL of dry ethanol, pyridine (1.32 mL, 0.015 mol), hydroxyl aminehydrochloride (0.71 g, 0.010 mol) was taken in a RB flask. The RM was refluxed for 3 hrs. Then the RM was poured into ice cold water and the precipitate obtained was filtered. Solid was subjected to column chromatography using hexane/ethyl acetate mixtures. The fraction obtained on elution with 35% of hexane/ethyl acetate to N-(3-oxime-11-keto-β-boswelloyl)-ammonia (57). [Yield—610 mg; Percentage yield was 74.4%]. $^1$H-NMR (CDCl$_3$): δ 8.13 (1H, brs), 5.56 (2H, s), 5.39 (1H, brs), 3.34 (1H, ddd, J=2.4, 6.4, 15.6 Hz), 2.92 (1H, ddd, J=2.4, 6.0, 14 Hz), 2.33 (1H, s), 2.23 (2H, m), 2.08 (1H, dt, J=4.0, 13.2 Hz), 1.92 (2H, m), 1.66 (1H, m), 1.58 (1H, m), 1.56 (2H, m), 1.53 (1H, m), 1.47 (3H, s), 1.40 (2H, m), 1.32 (3H, s), 1.30 (2H, m), 1.27 (3H, s), 1.23 (3H, s), 1.20 (1H, s), 1.14 (2H, m), 1.11 (1H, m), 1.05 (1H, m), 0.94 (3H, s), 0.82 (3H, s), 0.79 (3H, d, J=6.4 Hz). LCMS (m/z): 505 (M+Na)$^+$.

Example 31

Preparation of methyl 3-acetylamino-11-keto-urs-12-en-24-oate (58)

Step 1: Preparation of methyl ester of 3-hydroxy-11-keto-beta-boswellic acid

A mixture of 3-hydroxy-11-keto-beta-boswellic acid (6 g), 6 ml of thionyl chloride was taken in a RB flask. RM was refluxed for 1 hr. then it was dried under high vacuum. Then it was dissolved in 30 ml methanol and it was refluxed for 4 hrs. Then RM was concentrated, subjected to column chromatography. Product was eluted in 10% of hexane/ethyl acetate. [Yield—5.8 g: % of yield 94].

Step 2: Oxidation of methyl ester of 3-hydroxy-11-keto-beta-boswellic acid

A mixture of methyl ester 3-hydroxy-11-keto-beta-boswellic acid [5 g, 0.010 mol], 100 mL of MDC was taken in a RB. Jone's reagent (15 mL of Jone's reagent adsorbed with 30 g of silica gel) was slowly added to the reaction mixture at RT. After 1 h, the RM was filtered, washed with methylene dichloride. The organic layer was concentrated and the residue subjected to column chromatography on silica. Product was eluted in 20% of hexane/ethyl acetate. [Yield 3.2 g, percentage of yield was 64%].

Step 3: Preparation of 3-Oxime methyl ester of 3-hydroxy-11-keto-beta-boswellic acid A mixture of 3-keto methyl ester of 3-hydroxy-11-keto-beta-boswellic acid [3.0 g, 0.00622 mol] obtained above, 60 mL of dry ethanol, pyridine (5 mL, 0.06 mol), hydroxyl aminehydrochloride (2.59 g, 0.037 mol) was taken in a RB flask. The RM was refluxed for 3 hrs. Then the RM was poured into ice cold water and the solid obtained was filtered. The solid was subjected to column chromatography on silica using hexane/ethyl acetate mixtures. The product was eluted with 15% of hexane/ethyl acetate [Yield—2.3 g; Percentage yield 76.6%].

Step 4: Reduction of 3-Oxime methyl ester of 3-hydroxy-11-keto-beta-boswellic acid A mixture of 3-Oxime methyl ester of 3-hydroxy-11-keto-beta-boswellic acid [1.5 g] obtained above, 35 mL of ethanol, 10 mL of tetrahydrofuran (THF). 2 g of Raney nickel was slowly added and the RM stirred at RT under hydrogen atmosphere for 3 hrs. Then RM was filtered, the solid washed with ethanol, filtrate was concentrated [Yield—1.4 g].

Step 5: Acetylation of 3-amino methyl ester of 3-hydroxy-11-keto-beta-boswellic acid A mixture of 3-amino-11-keto-beta-boswellic acid ester (1.6 g), 5 mL of acetic anhydride was taken in RB flask. RM was stirred at 80° C. for 2 hrs. Then RM was poured into ice cold water, extracted with EtOAc, organic layer was washed with water, followed by brine. The organic layer was dried over Na$_2$SO$_4$ and concentrated. The residue was purified over silica column using acetone/chloroform mixtures. The fraction obtained on elution with 5% acetone/chloroform yielded methyl 3-acetylamino-11-ketours-12-en-24-oate (58). [Yield 710 mg, percentage of yield—41.7]. $^1$H-NMR (CDCl$_3$): δ 8.00 (1H, brs), 5.77 (1H, brs), 3.6 (3H, s), 2.53 (1H, m), 2.42 (1H, s), 2.3 (2H, m), 2.08 (3H, s), 1.96 (2H, m), 1.90 (1H, m), 1.78 (2H, m), 1.55-1.47 (6H, m), 1.37 (2H, m), 1.34 (3H, s), 1.31 (2H, m), 1.19 (3H, s), 1.14 (3H, s), 1.10 (3H, s), 1.04 (1H, m), 0.94 (3H, s), 0.93 (2H, m), 0.82 (3H, s), 0.8 (3H, d, J=6.4 Hz). LCMS (m/z): 526 (M+H)$^+$.

Formula-II

Analogs Preparation

Example 32

Preparation of 11-chloro-9-en-β-boswellic acid (59)

Step 1: Preparation of 11-chlorodiene of 3-O-acetyl-11-keto-boswellic acid

A mixture of 3-O-acetyl-11-keto-β-boswellic acid (5 g, 0.0097 mol), 3 mL of chloroform taken in a round bottom flask. Then phosphorous pentachloride (16 g; 0.078 mol) was added to reaction mixture (RM) at Room temperature. RM was stirred at 50° C. for 1 hr, then stirred at RT for 4 hours. Then RM was poured in ice cold water, extracted with Ethyl acetate (EtOAc), organic layer was washed with brine, dried over sodium sulphate and concentrated. The crude was subjected to column chromatography, hexane/acetone as an eluent. Compound eluted in 15% acetone in hexane. [Yield 2 g; Percentage of yield is 39.2%].

Step 2: Hydrolysis of 11-chlorodiene of 3-O-acetyl-11-keto-boswellic acid

A mixture of 11-chlorodiene of 3-O-acetyl-11-keto-boswellic acid (2 g) was dissolved in 8 mL of methanol. 4 ml of 8N KOH solution was added to RM. Then RM was stirred at 90° C. for 2 hrs. Then RM was poured into ice cold water, acidified with 5N HCl, solid was formed and it was filtered. The solid was washed with water and dried. Crude was subjected to column chromatography. The fraction obtained on elution in 20% acetone in hexane yielded 11-chloro-9-en-β-boswellic acid (59). [Yield—1.6 g, percentage of yield—86]. $^1$H-NMR (CDCl$_3$): δ 5.39 (1H, s), 4.46 (1H, s), 3.8 (1H, s), 3.00 (1H, m), 1.85-1.65 (6H, m), 1.55-1.47 (5H, m), 1.37 (2H, m), 1.31 (2H, m), 1.22 (3H, s), 1.19 (3H, s), 1.14 (3H, s), 0.98 (3H, s), 1.04 (1H, m), 0.94 (3H, s), 0.93 (2H, m), 0.82 (3H, s), 0.8 (3H, d, J=6.4 Hz). LCMS (m/z): 487 (M−H)$^+$.

Example 33

Preparation of 3-O-acetyl-11-chloro-9-en-β-boswellic acid (60)

A solution of 3-O-acetyl-11-keto-β-boswellic acid (5 g, 0.0097 mol) in 3 mL of chloroform in a round bottom flask was treated with phosphorous pentachloride (16 g; 0.078 mol) at Room temperature. The reaction mixtures (RM) was stirred at 50° C. for 1 hr and then stirred at RT for 4 hours. Then RM was poured in ice cold water and extracted with ethyl acetate (EtOAc). The organic layer was washed with brine, dried over sodium sulphate and concentrated. The crude mixture was subjected to column chromatography over silica using hexane/acetone mixtures as eluants. The fraction eluted with 15% acetone in hexane yielded 3-O-acetyl-11-chloro-9-en-β-boswellic acid (60). [Yield 2 g; Percentage of yield is 39.2%]. $^1$H-NMR (CDCl$_3$): δ 5.41 (1H, s), 5.12 (1H, s), 3.00 (1H, m), 2.01 (3H, s), 1.85-1.65 (6H, m), 1.55-1.47 (5H, m), 1.37 (2H, m), 1.31 (2H, m), 1.22 (3H, s), 1.20 (3H, s), 1.14 (3H, s), 0.97 (3H, s), 0.92 (3H, s), 0.82 (3H, s), 0.8 (3H, d, J=6.4 Hz). LCMS (m/z): 529 (M−H)$^+$.

Example 34

Preparation of N-(3-O-acetyl-11-chloro-9-en-β-boswelloyl)-ethylenediamine (61)

A mixture of 3-O-acetyl-11-chloro-9-en-β-boswellic acid (500 mg, 0.976 mmol) and 0.5 mL of SOCl$_2$ was taken in a RB and the mixture heated at 90° C. for 1 h. Excess SOCl$_2$ was evaporated and the residue dried under high vacuum. The residue was dissolved in 5 mL of methylene dichloride and treated with 50 mg of DMAP and ethylene diamine (0.39 mL, 5.85 mmol). The RM was stirred at RT for overnight. The mixture was was poured into ice cold water and extracted with EtOAc. The organic layer was washed with brine. dried over Na$_2$SO$_4$ and evaporated under vacuum. The residue was purified over silica column using methanol/CHCl$_3$ mixtures. The fraction eluted with 10% methanol/chloroform yielded N-(3-O-acetyl-11-chloro-9-en-β-boswelloyl)-ethylenediamine (61). [Yield: 360 mg; % of yield is 64.5]. $^1$H-NMR (CDCl$_3$): δ 8.10 (1H, d, J=6.0 Hz), 5.41 (1H, s), 5.12 (1H, s), 3.42 (2H, m), 2.94 (2H, m), 2.62 (1H, t, J=6.4 Hz), 2.16 (1H, m), 2.00 (3H, s), 1.95 (1H, m), 1.85-1.65 (7H, m), 1.55-1.47 (6H, m), 1.37 (2H, m), 1.31 (2H, m), 1.22 (3H, s), 1.15 (3H, s), 1.10 (3H, s), 0.97 (3H, s), 0.92 (3H, s), 0.82 (3H, s), 0.8 (3H, d, J=6.4 Hz). LCMS (m/z): 573 (M+H)$^+$.

Example 35

Preparation of N-(3-O-acetyl-11-chloro-9-en-β-boswelloyl)-hydrazine (62)

A mixture of 3-O-acetyl-11-chloro-9-en-β-boswellic acid (500 mg, 0.0.976 mmol) and 0.5 mL of SOCl$_2$ was taken in a RB and the mixture heated at 90° C. for 1 h. Excess SOCl$_2$ was evaporated and the residue dried under high vacuum. The residue was dissolved in 5 mL of methylene dichloride and treated with 50 mg of DMAP and hydrazine hydrate (0.141 mL, 2.82 mmol) and the mixture was stirred at RT for overnight. Then RM was poured into ice cold water and extracted with EtOAc. The organic layer was washed with brine, dried over Na$_2$SO$_4$ and evaporated under vacuum. The residue was chromatographed over silica using methanol/CHCl$_3$ mixtures. The fraction eluted with 10% methanol/chloroform yielded N-(3-O-acetyl-11-chloro-9-en-β-boswelloyl)-hydrazine (62). [Yield: 270 mg; % of yield is 47.3]. $^1$H-NMR (CDCl$_3$): δ 8.61 (1H, s), 5.46 (1H, s), 5.24 (1H, s), 4.43 (1H, brs), 3.02 (1H, m), 2.05 (3H, s), 1.94 (1H, s), 1.85-1.65 (6H, m), 1.55-1.47 (5H, m), 1.37 (2H, m), 1.34 (3H, m), 1.31 (2H, m), 1.27 (3H, s), 1.14 (3H, s), 1.02 (3H, s), 0.97 (3H, s), 0.86 (3H, s), 0.85 (3H, s), 0.8 (3H, d, J=6.4 Hz). LCMS (m/z): 543 (M−H)$^+$.

Example 36

Preparation of N-(3-O-acetyl-11-chloro-9-en-β-boswelloyl)-piperazine (63)

A mixture of 3-O-acetyl-11-chloro-9-en-β-boswellic acid (500 mg, 0.0.976 mmol) and 0.5 mL of SOCl$_2$ was taken in a RB and the mixture heated at 90° C. for 1 h. Excess SOCl$_2$ was evaporated and the residue dried under high vacuum. The residue was dissolved in 5 mL of methylene dichloride and treated with 50 mg of DMAP and piperazine (243 mg, 2.83 mmol) and the mixture was stirred at RT for overnight. The RM was poured into ice cold water and extracted with EtOAc. The organic layer was washed with brine, dried over Na$_2$SO$_4$ and concentrated under vacuum. The residue was chromatographed over silica gel using methanol/CHCl$_3$ mixtures. The fraction eluted with 5% methanol/chloroform yielded N-(3-O-acetyl-11-chloro-9-en-β-boswelloyl)-piperazine (63). [Yield: 300 mg; % of yield is 53.5]. $^1$H-NMR (CDCl$_3$): δ 5.41 (1H, s), 5.34 (1H, s), 3.46 (4H, m), 2.90 (1H, m), 2.68 (4H, brs), 2.05 (3H, s), 1.94 (1H, s), 1.85-1.65 (6H, m), 1.55-1.47 (5H, m), 1.37 (2H, m), 1.34 (3H, m), 1.31 (2H, m), 1.27 (3H, s), 1.14 (3H, s), 1.02 (3H, s), 0.97 (3H, s), 0.86 (3H, s), 0.85 (3H, s), 0.8 (3H, d, J=6.4 Hz). LCMS (m/z): 599 (M+H)$^+$.

Example 37

5-lipoxygenase inhibitory activity of novel boswellic acid analogs

5-Lipoxygenase enzyme inhibitory activity was measured using the method of Schewe et al. (Adv Enzymol, Vol 58, 191-272, 1986), modified by Reddanna et. al., (Methods of Enzymology, Vol 187, 268-277, 1990). The assay mixture contained 80 μM linoleic acid and sufficient amount of potato 5-lipoxygenase in 50 mM phosphate buffer (pH 6.3). The reaction was initiated by the addition of enzyme buffer mix to linoleic acid and the enzyme activity was monitored as the increase in absorbance at 234 nm. The reaction was monitored for 120 sec and the inhibitory potential of the test substances (29, 31, 33, 34, 35, 36, 39, 40, 43, 44, 46, 47, 48, 49, 50, 54, 57, 59, 62 & 63) was measured by incubating various concentrations of test substances two minutes before the addition of linoleic acid. All assays were performed three times. Percentage inhibition was calculated by comparing the slope of the curve obtained for test substances with that of the control. The 5-lipoxygenase inhibitory potential at 10 μg/ml and 25 μg/ml concentration is summarized in table-1.

TABLE 1

| Analog No. | % inhibition at 10 μg/ml | % inhibition at 25 μg/ml |
|---|---|---|
| 29. | 33.29 | N/A |
| 31. | 18.57 | 36.73 |
| 33. | 24.66 | 52.98 |
| 34. | 16.31 | 29.40 |
| 35. | 24.92 | 52.48 |
| 36. | 17.83 | 34.40 |
| 39. | 32.11 | 48.69 |
| 40. | 18.40 | 40.47 |
| 43. | 14.57 | 30.90 |
| 44. | 19.88 | 30.02 |
| 46. | 19.01 | 30.56 |
| 47. | 35.94 | 54.10 |
| 48. | 22.78 | 54.18 |
| 49. | 31.55 | 47.02 |
| 50. | 18.94 | 38.85 |
| 54. | 35.69 | 64.24 |
| 57. | 14.32 | 28.45 |
| 59. | 21.46 | 39.24 |
| 62. | 36.26 | N/A |
| 63. | 36.20 | 57.86 |

Example 38

The Potential In Vitro Inhibitory Effects of a Few Selected Analogs were Put to Test In Vivo Against Freund's Adjuvant-Induced Arthritis in Wistar Albino Rats The Wistar Albino rats were divided into four groups with four animals each group. The two treatment groups, each containing 6 animals, were orally supplemented with one of the two analogs namely glycinate of AKBA (10) or piperazine amide of AKBA (23) in 1% carbomethylcellulose (CMC) at a daily dose of 10 mg/kg for 30 days. The control group of animals received same volume of 1% CMC orally and a positive control group received 10 mg/kg daily dose of prednisolone for direct comparison. Following the 30 day treatment and one hour after the last dose all the animals were challenged with 0.1 mL of 1% solution of Freund's Adjuvant through a subcutaneous injection in the sub-plantar region of left hind paw. The paw volume was measured using a plethymograph. The difference between the paw volumes measured before and 13 days after the Freund's Adjuvant injection was taken as edema volume. The percentage inhibition was calculated by comparing the mean edema of the control group and treatment groups. The positive control prednisolone exhibited 16.8% inhibition of paw edema, whereas boswellic acid analogs 10 and 23 showed 12% and 16.4% inhibitions respectively.

Example 39

LI-51255 (21) Inhibits VEGF Production in Human Endothelial Cells

Methods

Equal number of HUVEC human primary endothelial cells was plated in 35 mm culture dishes. The cells exposed to either 0.5% DMSO as vehicle or LI-51255 for 24 h. The cells were lysed in cell lysis buffer. The protein concentration of each lysate was determined by the BCA method (BioRad, Hercules, Calif.). Equal amount of cell lysates proteins was resolved in SDS-PAGE and the transferred proteins on nitrocellulose membrane were reacted with human anti-VEGF antibody (Cell Signaling Technology, Beverly, Mass.) overnight at 4° C. Immunoreactive proteins were detected using were developed with Super SignalWest Pico Chemiluminescent substrate (Pierce Biotechnology Inc.) and the band intensities were analyzed using Molecular Imaging Software, version 4.0 (Eastman Kodak Company, Rochester, N.Y.). Relative density was determined by normalization of the density of each blot with that of corresponding β-actin. Comments: LI-51255 inhibits expression of VEGF in human endothelial cells which indicates that LI-51255 might suppress angiogenesis in tumor cells. The data is summarized in FIG. IA.

Example 40

LI-51255 (21) Inhibits Capillary-Like Tube Formation

Method:

In vitro capillary formation assay was performed with Human umbilical vein endothelial cells (HUVEC), cultured on 10 mg/ml basement membrane extract (BME—Cultrex®, R&D Systems, USA) bed. The protocol of in vitro endothelial tube formation assay was the same as described earlier with some modifications (Reference). Briefly, four hundred microliters of Cultrex was coated at 4° C. in each well of 24-well culture plate and allowed to gel at 37° C. for 1 h. HUVECs were plated at a density of $7.5 \times 10^4$ cells per well with 400 µl of DMEM supplemented with 10% fetal bovine serum and 4.5 g/l D-glucose. The cells were then treated with either 0.5% DMSO or different concentrations of LI-51255 for 16 hours. Pictures were taken under a Nikon Eclipse TS 100 microscope equipped with a Nikon Coolpix camera (FIG. 1B).

Comments:

LI-51255 exhibited dose-dependent inhibition of human endothelial capillary formation in vitro. This observation indicates that LI-51255 might inhibit angiogenesis process, which could be a potential strategy for controlling tumor growth by inhibiting or blocking blood circulation to the tumor tissue.

Example 41

Anti-Tumor Growth Potential of Some Analogs in Breast, Lung Cancer and Melanoma Cell Line MTT [3-(4,5-dimethylthiazol-2-yl)-2,5-diphenyltetrazolium bromide] incorporation based cell proliferation assay was performed as described previously (Reference). The cytotoxic efficacy of some analogs was evaluated in different cell lines by MTT cell proliferation assay kit (Roche Applied Sciences, Germany). The assay was carried out according to the instruction provided by the vendor. Briefly, in brief, equal numbers of cells was plated in 96-well flat-bottomed plates in 100 µl of medium and were exposed to different analogs selected from 1 to 63 at various concentrations up to 10 µg/ml for a period of three days. Vehicle control culture wells received only a maximum of 0.5% DMSO. Thereafter, 0.5 mg/ml of MTT reagent was added to each well and the microplate was incubated further for 4 h at 37° C. in presence of 5% CO2. Finally, the cells were solubilized by adding solubilizing solution and allowed to incubate at 37° C. overnight. After complete solubilization of the formazan crystals the absorbance was read at 540 nm in a microplate reader (BioRad, USA). The results (mean OD±SD) obtained from quadruplicate wells were used in calculation to determine the inhibition of cell proliferation (50% of inhibitory concentration, IC50) of the test compounds. The data is tabulated in Table-2.

TABLE 2

| Analog No. | Inhibition of cell proliferation | | | | |
|---|---|---|---|---|---|
| | MDA-MB-231 | MCF-7 | A549 | A375 | B16 |
| 48. | 4.98 ug/ml (IC50) | 12.5 ug/ml (IC50) | 6.83 ug/ml (IC50) | 3.53 ug/ml (IC50) | 4.35 ug/ml (IC50) |
| 28. | 4.44 ug/ml (IC50) | 11.7 ug/ml (IC50) | 5.59 ug/ml (IC50) | 1.96 ug/ml (IC50) | 2.44 ug/ml (IC50) |
| 29. | 36% at 10 ug/ml | 38.3% at 10 ug/ml | — | — | — |
| 30. | 35% at 10 ug/ml | 46% at 10 ug/ml | 18% at 10 ug/ml | — | NA at 10 ug/ml |
| 31. | 46% at 10 ug/ml | NA at 10 ug/ml | 17% at 10 ug/ml | — | 10% at 10 ug/ml |
| 32. | 41% at 10 ug/ml | 14% at 10 ug/ml | 10% at 10 ug/ml | — | NA at 10 ug/ml |
| 33. | NA at 10 ug/ml | 36% at 10 ug/ml | 24% at 10 ug/ml | — | 9.1 ug/ml (IC50) |
| 34. | 6.38 ug/ml (IC50) | 13.7 ug/ml (IC50) | 10.5 ug/ml (IC50) | 4.12 ug/ml (IC50) | 3.84 ug/ml (IC50) |
| 35. | 5.14 ug/ml (IC50) | 9.7 ug/ml (IC50) | 5.86 ug/ml (IC50) | 2.76 ug/ml (IC50) | 2.82 ug/ml (IC50) |

TABLE 2-continued

| Analog No. | Inhibition of cell proliferation | | | | |
|---|---|---|---|---|---|
| | MDA-MB-231 | MCF-7 | A549 | A375 | B16 |
| 36. | 3.4 ug/ml (IC50) | 8.7 ug/ml (IC50) | 4.78 ug/ml (IC50) | 2.75 ug/ml (IC50) | 2.44 ug/ml (IC50) |

Example 42

Determination of Cytotoxicity of Boswellia Analogs Using MTT Assay

The cytotoxic properties of some analogs were evaluated by MTT incorporation assay. The methodology of the assay procedure was the same as mentioned in example 41. The minimum inhibitory concentration (MIC) data is summarized in Table-3.

TABLE 3

| Analog No. | Jurkat | $PC_{3M}$ | $HePG_2$ |
|---|---|---|---|
| 2 | 75 | 100 | >150 |
| 3 | 125 | 30 | 150 |
| 10 | 50 | 50 | >150 |
| 11 | 50 | 30 | 100-150 |
| 16 | 10 | >150 | >150 |
| 19 | 10 | >150 | >150 |
| 20 | 50 | 10 | 40 |
| 23 | 50 | 10 | 40 |
| 25 | 50 | 30 | 50 |

Example 43

Determination of Cytotoxicity of Boswellia Analogs (Disclosed in Earlier Application) in Melanoma Cell Lines Using MTT Assay The cytotoxic properties of some analogs were evaluated by MTT incorporation assay. The methodology of the assay procedure was the same as mentioned in example 41.

TABLE 4

| Analog No. | Percentage Inhibition of cell proliferation/ IC50 values | |
|---|---|---|
| | MCF-7 | MDA-MB-231 |
| 4 | 26.6% at 10 µg/ml | 40.7% at 10 µg/ml |
| 10 | IC50 at 26.89 µg/ml | IC50 at 19.5 µg/ml |
| 11 | IC50 at 33.33 µg/ml | IC50 at 28.93 µg/ml |
| 15 | 21.6% at 10 µg/ml | 37.5% at 10 µg/ml |
| 16 | 21% at 10 µg/ml | 47.12% at 10 µg/ml |
| 18 | 5.97 at 10 µg/ml | — |
| 19 | IC50 at 30.05 µg/ml | 38.72% at 10 µg/ml |
| 20 | 44% at 10 µg/ml | — |
| 21 | IC50 at 12.98 µg/ml | IC50 at 3.45 µg/ml |
| 23 | IC50 at 9.03 µg/ml | IC50 at 5.53 µg/ml |
| 25 | IC50 at 13.98 µg/ml | IC50 at 13.19 µg/ml |
| 28 | 34.26% at 10 µg/ml | 41.26% at 10 µg/ml |
| 29 | 38.3 at 10 µg/ml | 36% at 10 µg/ml |
| 30 | 46% at 10 µg/ml | 35% at 10 µg/ml |
| 31 | — | 46% at 10 µg/ml |
| 32 | 14% at 10 µg/ml | 41% at 10 µg/ml |
| 33 | 36% at 10 µg/ml | — |
| 34 | IC50 at 13.7 µg/ml | IC50 at 6.38 µg/ml |
| 35 | IC50 at 9.7 µg/ml | IC50 at 5.14 µg/ml |
| 36 | IC50 at 8.7 µg/ml | IC50 at 3.4 µg/ml |
| 37 | — | 23% at 10 µg/ml |
| 38 | 2.73% at 10 µg/ml | 20% at 10 µg/ml |
| 40 | 2.7% at 10 µg/ml | 31% at 10 µg/ml |
| 41 | 3.74% at 10 µg/ml | 23% at 10 µg/ml |
| 42 | 2.33% at 10 µg/ml | 6% at 10 µg/ml |
| 43 | 12.6% at 10 µg/ml | 47.84% at 10 µg/ml |
| 44 | IC50 at 24.06 µg/ml | IC50 at 28.65 µg/ml |
| 45 | IC50 at 11.88 µg/ml | IC50 at 11.96 µg/ml |
| 46 | 39% at 10 µg/ml | — |
| 47 | 10% at 10 µg/ml | 39% at 10 µg/ml |
| 48 | — | 8.8% at 10 µg/ml |
| 49 | 40.9% at 10 ug/ml | 21.4 at 10 µg/ml |
| 50 | 20.3% at 10 ug/ml | 16.5% at 10 µg/ml |
| 51 | IC50 at 9.27 µg/ml | IC50 at 10.5 µg/ml |
| 55 | IC50 at 8.79 µg/ml | IC50 at 7.31 µg/ml |
| 56 | 20% at 10 µg/ml | 47% at 10 µg/ml |
| 57 | — | 25.8% at 10 µg/ml |
| 61 | 41% at 10 µg/ml | IC50 at 8.55 µg/ml |

IC50 indicates the inhibitory concentration of the test compound required for inhibiting 50 percent of the tumor or cancer cells.

Example 44

Inhibition of PI3K Pathway by Analog LI-51255 by Down Regulating AKT Phosphorylation in Human Metastatic Breast Tumor Cells Methods:

Equal number of MDA-MB-231 human breast tumor cells (ER-) was plated in 25 $cm^2$ cell culture flasks. The cells treated with either 0.5% DMSO as vehicle or 10 µg/ml of LI-51255 for 0, 5, 10, 20, 30, 60, 120 and 240 min. The cells were lysed in cell lysis buffer. The protein concentration of each lysate was determined by the BCA method (BioRad, Hercules, Calif.). Equal amount of cell lysates proteins was resolved in SDS-PAGE and the transferred proteins on nitrocellulose membrane were reacted with AKT, phospho-AKT (ser473) and phospho-raf (ser259) antibodies (Cell Signaling Technology, Beverly, Mass.) overnight at 4° C. Immunoreactive proteins were detected using were developed with Super SignalWest Pico Chemiluminescent substrate (Pierce Biotechnology Inc.) and the band intensities were analyzed using Molecular Imaging Software, version 4.0 (Eastman Kodak Company, Rochester, N.Y.). Comments: LI-51255 deactivates AKT pathway in MDA-MB-231 human breast tumor cells which indicates that LI-51255 inhibits cell proliferation and metastatic growth of the tumor cells. The data is summarized in FIG. II.

Example 45

Anti-Tumor Growth Potential of Some Analogs of LI-51255 Inhibits Human Breast Tumor Cells MDA-MB-231 Clone Formation In Vitro Methods:

Inhibitory efficacy in clone formation of LI-51255 was tested by following the procedure described earlier with some modifications (Wu et al. 2005). Briefly, MDA-MB-231 cells were harvested and seeded into 6-well plates (100 cells/ml). The cells were allowed to grow for 4 days and thereafter, the cells were incubated with DMEM containing either 0.5% DMSO or 25 µg/ml AKBA or different concentrations (1.0, 1.5, 2.0, 2.5 µg/ml) of LI-51255 for further 8 days. Fresh medium containing test agents was replaced at every 24 h. Finally, the wells were washed three times with PBS and fixed in methanol for 15 min. The cells were stained with Giemsa stain and observed under microscope. The image of the stained wells were captured digitally (Kodak Image Station 4000MM, Carestream Health Inc., New Haven, Conn.) and number of colonies were counted and analyzed by using NIH Image J software.

Comments:

The observation indicates that LI-51255 potentially inhibits the growth and development of MDA-MB-231 breast tumor colonization in vitro. The data is summarized in FIG. III.

Example 46

Interruption of Cell Cycle at subG1 Phase in B16 Murine Melanoma Cells by LI-51255

Methods:

MDA-MB-231 cells were treated with LI-51255 for 24 h, vehicle control culture received only 0.5% DMSO. For flow cytometry, cells were harvested after the treatment period, washed with phosphate buffered saline (PBS), and adjusted the cell count at $2\times10^6$ cells per milliliter. The cells were fixed in 70% ethanol for 30 min at 4° C. Cells were then washed two times with PBS and stained with 0.5 µg/ml propidium iodide at 37° C. for 30 min and analyzed by flow cytometry. Data were acquired on a FACS Scan flow cytometer (Becton Dickinson) and analyzed by using the Cellquest software.

Comments:

The data indicates that LI-51255 arrests the growth of B16 murine melanoma cells at the subG1 phase of cell cycle. The data is summarized in Table-5.

TABLE 5

| LI-51255 (mg/ml) | Sub $G_1$ | $G_1$ | S | $G_2$/M |
|---|---|---|---|---|
| 0 | 1.19 | 74.02 | 12.12 | 12.65 |
| 5 | 1.7 | 74.74 | 11.18 | 12.2 |
| 10 | 19.76 | 60.25 | 10.87 | 9.19 |

Example 47

Reduction of Melanoma Tumor Burden in B16 F0 Xenograft Model of C57 B6J Mice by LI-51255

Methods:

In vivo efficacy of LI-51255 against melanoma growth was evaluated in B16 F0 melanoma xenograft model of C57B6J mice. C57B6J mice of 6 weeks age (body weight 18-22 g) were purchased from National Institute of Nutrition (NIN), Hyderabad (India). Animals study protocols were approved by Institutional Ethics Committee (IAEC). All the studies were performed in compliance with the Committee for the Purpose of Control and Supervision of Experiments on Animals (CPCSEA) guidelines and OECD guidelines. Animals were allowed free access to standard feed and provided charcoal filtered and UV exposed water ad libitum. The animals were maintained at a controlled temperature (24-26° C.), humidity (45-70%), and 12 h/12 h of light/dark cycle.

To induce the melanoma tumor formation, sub-confluent B16F0 cells were harvested by brief trypsinization and $1\times10^6$ cells were injected subcutaneously in 0.2 mL phosphate-buffered saline. Drug treatment was started after development of palpable tumors (3-5 days after implantation of the cells). Drugs were prepared in phosphate-buffered saline (10% DMSO, v/v) and either 75 mg/kg of DTIC or different doses of LI-51255 (10 or 20 mg/kg) was administered daily through intra-peritoneal route. Vehicle treated control animals received only 10% DMSO in phosphate buffered saline. After twelve days of treatment, the animals were sacrificed by $CO_2$ inhalation and tumors were excised and weighed. Table-6 shows efficacy of inhibiting tumor growth by LI-51255 in comparison with DTIC in B16 F0 melanoma xenograft model of C57B6J mice.

TABLE 6

| Groups | Average weight of tumor (in gm) | SD | % reduction of tumor burden(w.r.t control) | t-test (vs. control) |
|---|---|---|---|---|
| Control (10% DMSO in HBSS) | 6.289 | 1.237 | — | — |
| LI-51255 (10 mg/kg) | 4.575 | 1.432 | 27.253 | 0.0182 |
| LI-51255 (20 mg/kg) | 3.050 | 1.184 | 51.502 | 0.0001 |
| DTIC (75 mg/kg) | 4.175 | 2.338 | 33.613 | 0.0316 |

The invention claimed is:
1. A compound having the formula I:

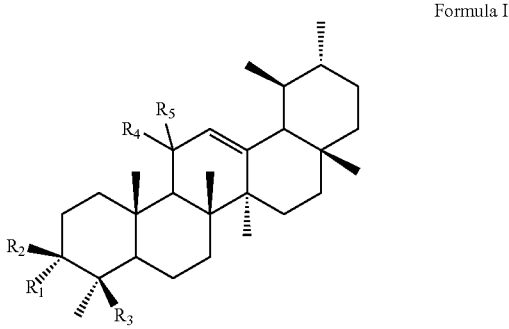

Formula I wherein $R_1$, $R_2$, $R_3$, $R_4$ and $R_5$ are as indicated in one of the following combinations:

$R_1$=OCOCH$_3$, $R_2$=H, $R_3$=CON(CH(CH$_3$)$_2$)$_2$, $R_4$ & $R_5$=O;
$R_1$=OCOCH$_3$, $R_2$=H, $R_3$=CONHCH$_2$CH$_2$CH$_2$CH$_3$, $R_4$ & $R_5$=O;
$R_1$=OCOCH$_3$, $R_2$=H, $R_3$=CONHCH(CH$_3$)$_2$, $R_4$ & $R_5$=O;
$R_1$=OCOCH$_3$, $R_2$=H, $R_3$=CON(CH$_3$)$_2$, $R_4$ & $R_5$=O;
$R_1$=OCOCH$_3$, $R_2$=H, $R_3$=CONHCH$_2$COOCH$_3$, $R_4$ & $R_5$=O;
$R_1$=OCOCH$_3$, $R_2$=H, $R_3$=CONHCH$_2$(CH$_2$)$_4$CH$_2$NH$_2$, $R_4$ & $R_5$=O;
$R_1$=OCOCH$_3$, $R_2$=H, $R_3$=CONHCH$_2$(CH$_2$)$_2$CH$_2$NH$_2$, $R_4$ & $R_5$=O;
$R_1$=OCOCH$_3$, $R_2$=H, $R_3$=CONHCH$_2$(CH$_2$)$_5$CH$_2$NH$_2$, $R_4$ & $R_5$=O;
$R_1$=OH, $R_2$=H, $R_3$=CON(CH$_2$CH$_2$)$_2$O, $R_4$ & $R_5$=O;
$R_1$=OCOCH$_3$, $R_2$=H, $R_3$=CON(CH$_2$CH$_2$)$_2$O, $R_4$ & $R_5$=O;
$R_1$=OH, $R_2$=H, $R_3$=CON(CH$_2$CH$_2$)$_2$NCH$_2$CH$_2$OH, $R_4$ & $R_5$=O;
$R_1$=OOCH$_3$, $R_2$=H, $R_3$=CON(CH$_2$CH$_2$)$_2$NCH$_2$CH$_2$OH, $R_4$ & $R_5$=O;
$R_1$=OCOCH$_3$, $R_2$=H, $R_3$=Imidazole-1-carbonyl, $R_4$ & $R_5$=O;

$R_1$=OCOCH$_3$, $R_2$=H, $R_3$=2-Aminoindane-N-carbonyl, $R_4$ & $R_5$=O;
$R_1$=OCOCH$_3$, $R_2$=H, $R_3$=CONHC$_6$H$_5$, $R_4$ & $R_5$=O;
$R_1$=OCOCH$_3$, $R_2$=H, $R_3$=CONHCH$_3$, $R_4$ & $R_5$=O;
$R_1$=OCOCH$_3$, $R_2$=H, $R_3$=CONH(2-C$_6$H$_4$Br), $R_4$ & $R_5$=O;
$R_1$=OCOCH$_3$, $R_2$=H, $R_3$=CON(CH$_3$)CH$_2$CH$_2$OH, $R_4$ & $R_5$=O;
$R_1$=OCOCH$_3$, $R_2$=H, $R_3$=CONH(p-C$_6$H$_4$OH), $R_4$ & $R_5$=O;
$R_1$=OCOCH$_3$, $R_2$=H, $R_3$=CONHNHC$_6$H$_5$, $R_4$ & $R_5$=O;
$R_1$=OCOCH$_3$, $R_2$=H, $R_3$=CONHCH$_2$CH$_2$NHCHO, $R_4$ & $R_5$=O;
$R_1$=OCOCH$_3$, $R_2$=H, $R_3$=CONHCH$_2$CH$_2$N(CH$_2$CH$_2$OH)$_2$., $R_4$ & $R_5$=O;
$R_1$=OCOCH$_3$, $R_2$=H, $R_3$=CONHCH$_2$CH$_2$NHCOCHCH(3,4-C$_6$H$_3$O$_2$CH$_2$), $R_4$ & $R_5$=O;
$R_1$=OCOCH$_3$, $R_2$=H, $R_3$=CONHCH$_2$CH$_2$NH$_2$, $R_4$ & $R_5$=H;
$R_1$=OCOCH$_3$, $R_2$=H, $R_3$=CONH$_2$, $R_4$ & $R_5$=H;
$R_1$=OCOCH$_3$, $R_2$=H, $R_3$=CONHCH$_2$CH$_2$OH, $R_4$ & $R_5$=H;
$R_1$=OCOCH$_3$, $R_2$=H, $R_3$=CON(CH$_2$CH$_2$)$_2$NH, $R_4$ & $R_5$=H;
$R_1$=OCOCH$_3$, $R_2$=H, $R_3$=CONHCH$_2$CH$_2$NHCH$_3$, $R_4$ & $R_5$=O;
$R_1$=OCOCH$_3$, $R_2$=H, $R_3$=CONHCH(COOCH$_3$)CH$_2$CH$_2$COOCH$_3$, $R_4$ & $R_5$=O;
$R_1$ & $R_2$=NOH, $R_3$=CONH$_2$, $R_4$ & $R_5$=O; and
$R_1$ & $R_2$=NHCOCH$_3$, $R_3$=COOCH$_3$, $R_4$ & $R_5$=O.

2. A compound having the formula II:

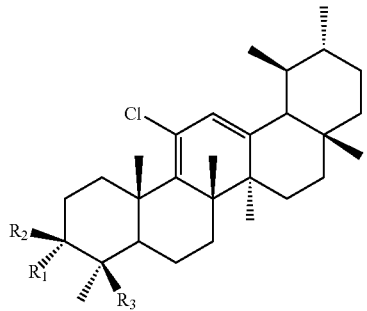

Formula II wherein $R_1$, $R_2$, $R_3$, $R_4$ and $R_5$ are as indicated in one of the following combinations:
$R_1$=OH, $R_2$=H, $R_3$=COOH;
$R_1$=OCOCH$_3$, $R_2$=H, $R_3$=COOH;
$R_1$=OCOCH$_3$, $R_2$=H, $R_3$=CONHCH$_2$CH$_2$NH$_2$;
$R_1$=OCOCH$_3$, $R_2$=H, $R_3$=CONHNH$_2$; and
$R_1$=OCOCH$_3$, $R_2$=H, $R_3$=CON(CH$_2$CH$_2$)$_2$NH.

* * * * *